(12) United States Patent
Spartiotis et al.

(10) Patent No.: US 7,136,452 B2
(45) Date of Patent: Nov. 14, 2006

(54) RADIATION IMAGING SYSTEM, DEVICE AND METHOD FOR SCAN IMAGING

(75) Inventors: Konstantinos E. Spartiotis, Espoo (FI); Markku Eräluoto, Espoo (FI)

(73) Assignee: Goldpower Limited, Tortola (VG)

( * ) Notice: Subject to any disclaimer, the term of this patent is extended or adjusted under 35 U.S.C. 154(b) by 389 days.

(21) Appl. No.: 10/024,037

(22) Filed: Dec. 21, 2001
(Under 37 CFR 1.47)

(65) Prior Publication Data

US 2004/0000630 A1    Jan. 1, 2004

Related U.S. Application Data

(63) Continuation-in-part of application No. 08/871,512, filed on Jun. 9, 1997, now abandoned, which is a continuation of application No. 08/454,789, filed on May 31, 1995, now Pat. No. 5,812,191.

(60) Provisional application No. 60/257,168, filed on Dec. 22, 2000.

(30) Foreign Application Priority Data

Dec. 22, 2000  (GB) ................... 0031542.4
Aug. 10, 2001  (GB) ................... 0119559.3

(51) Int. Cl.
*H05G 1/60* (2006.01)
*H05G 1/64* (2006.01)

(52) U.S. Cl. ............. 378/19; 378/98.8; 378/38; 250/370.09

(58) Field of Classification Search ........... 378/19, 378/38–40, 98.8, 37; 250/370.09
See application file for complete search history.

(56) References Cited

U.S. PATENT DOCUMENTS 4,636,980 A * 1/1987 Bluzer .................. 365/106
5,265,142 A * 11/1993 Hsieh .................... 378/4

(Continued)

FOREIGN PATENT DOCUMENTS

| GB | 2 289983 | 12/1995 |
|---|---|---|
| GB | 2 332 608 | 6/1999 |
| JP | 09 135829 | 5/1997 |

OTHER PUBLICATIONS

"USB 2.0- Hi-Speed USB- FAQ" Everything USB, http://www.entlink.net/education/resources, Printed Nov. 14, 2004.*

(Continued)

*Primary Examiner*—Edward J. Glick
*Assistant Examiner*—Krystyna Suchecki

(57) ABSTRACT

An imaging system for high energy radiation direct conversion scan imaging includes a high energy radiation source and a semiconductor high energy radiation direct conversion imaging device arranged around an object position. The imaging device includes a plurality of imaging cells, each imaging cell comprising a detector cell and a readout cell for producing imaging cell output values representative of high energy radiation incident on the detector cell. The source member and/or the imaging device were arranged to move substantially continuously relative to each other for scanning an object at the object position. The readout cells are operated to read out the imaging cell output values at time intervals which substantially correspond to an object image point traversing half the distance of a detector region or cell in the scanning direction. Such a configuration provides for pixel level resolution during the scanning operation.

64 Claims, 14 Drawing Sheets

U.S. PATENT DOCUMENTS

| | | | |
|---|---|---|---|
| 5,340,988 A | | 8/1994 | Kingsley et al. |
| 5,510,623 A | | 4/1996 | Sayag et al. |
| 6,134,298 A | * | 10/2000 | Schick et al. ............... 378/98.8 |
| 6,262,408 B1 | * | 7/2001 | Izumi et al. ............. 250/208.1 |
| 2002/0017609 A1 | * | 2/2002 | Danielsson ............ 250/370.09 |
| 2002/0018543 A1 | * | 2/2002 | Danielsson ................ 378/98.8 |

OTHER PUBLICATIONS

Allison D. et al. "A Novel Semiconductor Pixel Device and System for X-Ray and Gamma Ray Imaging", 1996, IEEE Nuclear Science Symposium. Conference Record, Anaheim, USA, vol. 2, 1996; pp. 1248-1250.

* cited by examiner

Panoramic X-ray imaging

Table 1 operating modes

| Mode 1,mode 0 | Start row | End row | Description |
|---|---|---|---|
| 0,0 | 1 | 108 | Whole chip |
| 0,1 | 15 | 94 | 8mm window |
| 1,0 | 25 | 84 | 6mm window |
| 1,1 | 35 | 74 | 4mm window |

Example schematic for using one tile

Example schematic for connecting two tiles as one

RADIATION IMAGING SYSTEM, DEVICE AND METHOD FOR SCAN IMAGING

CROSS REFERENCE TO RELATED APPLICATIONS

This application is a non-provisional application of U.S. provisional application Ser. No. 60/257,168 filed Dec. 22, 2000, and this application is a Continuation-In-Part of U.S. application Ser. No. 08/871,512 filed Jun. 9, 1997, now abandoned which is a continuation application of U.S. application Ser. No. 08/454,789, filed May 31, 1995 now U.S. Pat. No. 5,812,191.

The present invention relates to a high energy imaging system, device and method for scan imaging. In particular, but not exclusively, the invention relates to dental panoramic imaging systems, and automated X-ray inspection using in-line testing.

In traditional panoramic imaging, the X-ray source and the film cassette are located on opposite sides of the part of a patient's body to be imaged. For example, in panoramic imaging the X-ray source and film cassette are located on opposite sides of a patient's head. During an exposure, the X-ray source and the film cassette are rotated around the patient's head. Typically, the centre of rotation does not remain stationary but is also moved along a predefined path. The X-ray beam is collimated and is typically very narrow and therefore only a narrow part of the film is exposed at any time. The film cassette is also moved during the exposure. The speed of the rotation, the speed of the cassette movement and the X-ray intensity is varied during the exposure to compensate for the different X-ray absorption in different parts of the skull. The speed of the film cassette is chosen in a way that a wanted layer is projected to form a sharp final image. Panoramic imaging with a film cassette is illustrated in FIG. 1. The two positions for the X-ray source 2, X-ray beam 4 and the film cassette 3 are shown. This illustrates the rotating operation of a panoramic imaging system. The direction of rotation is shown with arrows. Also, the direction of film cassette movement and the movement of the centre of rotation are indicated with arrows.

As illustrated in FIG. 1, the object to be imaged, in this example a patient's head 1, is placed between an X-ray source 2 and a film cassette 3. The X-ray source 2 produces a narrow X-ray beam 4, which is typically termed a "fan beam". Both the X-ray source 2 and film cassette 3 are rotated about the patient's head 1 in the same direction. The axis of rotation 5, may also be moved in order to image a desired plane within the head 1. The X-ray beam 4 may be broader than is typical for a "fan beam", and such a configuration is often known as a "cone beam".

During rotation of the X-ray source 2 and film cassette 3, i.e. during scanning, the film itself is moved within the film cassette 3 in order to focus the desired image point in the desired plane onto the film. For tomographic imaging, image scans are obtained for different paths of the centre of rotation 5 thereby obtaining images of different planes which can be combined to form a tomographic or 3-dimensional image.

One limitation of this way of performing panoramic imaging is that only one tomographic plane is created in any one scan since only one plane stays in focus. All other planes are unfocussed and therefore blurred out during the scan. Thus, the rest of the object volume creates background noise, since it is only the projected plane that stays in focus.

The present invention finds application to imaging apparatus using semiconductor imaging devices and is suitable for high energy radiation imaging (i.e. radiation having energies in excess of 1 keV including such as α-rays, β-rays and γ-rays not just X-rays.

Traditional arrangements for X-ray imaging, including cassette film, and other modalities such as wire chambers, scintillating crystals or screens, (e.g. Sodium Iodide NaI), BGO (Bismuth Germanium Oxide) and CR plates (Computed Radiography), have been utilized over the past forty years.

More recently, semiconductor imaging devices have been employed, including CCD-based devices, both in stand-alone implementations and coupled to scintillating screens, silicon microstrip detectors and semiconductor pixel detectors.

A drawback of indirect X-ray conversion technologies, such as CCD-based devices combined with a scintillating screen, is that the resulting image lacks clarity and sharpness. This degradation in the resulting image is due to the visible light photons generated by X-rays incident on the scintillator spreading laterally through the scintillator material. Another drawback of such indirect systems is that the thickness of the scintillator material necessary to provide adequate X-ray to visible light conversion results in a relatively thick overall imaging device structure which prohibits, or at least inhibits, their use in applications for which small or low volume devices are necessary, e.g. applications such as dental intra-oral radiology where patient comfort and convenience is important.

A yet further drawback is that indirect imaging devices use the same electronic circuit or detector for both capturing the visible light photons, converting them to electrical signals and transferring the electrical signals for remote processing and image display. This result in dead image acquisition time during signal readout for conventional CCD indirect imaging devices, thereby preventing multiple frame readout during a single exposure since additional incoming radiation light would not be recorded in one to one correspondence with a pixel position during the readout process, and limiting the dynamic range.

Additionally, CCD devices are generally narrow and are kept stationary in scanning systems.

A CCD system operating as a scanning device operates in Time Delay Integration (TDI) mode. In this mode the contents of a pixel are shifted to an adjacent pixel in the opposite direction of scanning at time intervals to match the scanning speed. Thus effective integration of the incoming signal is achieved for the entire width of the CCD sensor. However this mode operation of CCD's necessary for scanning precludes multiple frame outputs and only one plane of the scanned object stays in focus as in the case of film. Thus, the digitally produced image has no more information than an image produced on film since neither can be filtered to reduce the noise produced from all the other object tomographic planes. This is the only way of operating a CCD sensor as a scanning device.

For Thin Film Transistor (TFT), photo diode or Active Pixel Sensors (APS), more commonly known as flat panels, the detector is aerial and it is not possible to read only specific rows or columns very fast. While in principle it could be possible to build a flat panel detector that suits the shape of a fan beam in reality it is not practical (too costly), and further more the poor noise performance would make it impossible to read out these sensors at high frame speed, e.g. at more than sixty frames per second.

Semiconductor pixel detectors, such as have been described in the Applicant's International patent application WO95/33332, based on ASIC (Application Specific Integrated Circuit) CMOS processing, can provide high spatial resolution, direct detection, compactness, high absorption efficiency and real-time imaging. Additionally, such pixel detectors are low profile since they do not require a scintillator layer. An example of a dental imaging device and system is described in "Development of a Compact Computed Tomographic Apparatus for Dental Use", Y, Arai, E Tammisalo, K. Iwai, K. Hashimoto and K. Shinoda, Dentomaxillofacial Radiology (1999) 28, 245–248, (Reference [1]). This document discloses computed tomographic apparatus for maxillofacial three dimensional imaging. An X-ray image intensifier is used as the detector instead of film, and irradiated with X-rays in a cone-beam arrangement. The X-ray source and image intensifier are placed either side of a patient's head, and rotated about the patient's head to provide a scanned image.

Each scan is over 360° and comprises approximately 572 sets of two dimensional projection data from which an image is reconstructed. An X-ray exposure is taken at each step to provide a series of two dimensional images.

Other examples of computed tomographic type systems are described in "Three-Dimensional Breast Image Reconstruction From a Limited Number of Views", Thomas G. McCauley, Alex Stewart Martin Stanton, Tao Wu and Walter Philips, Medical Imaging 2000: Physics of Medical Imaging, Proceedings of SPIE Vol. 3977 (2000), pp. 384–395) (Reference [2]). In Reference [2] a CCD based imaging system is disclosed for 3-D mammographic imaging with reduced data collection.

"Real Time Flat Panel Detector-Based Volume Tomographic Angiography Imaging: Detector Evaluation" Ruola Ning, Richard Colbeth, Biao Chen, Rongfeng Yu, David Conover, Yi Ning and Chuck Blouir, Medical Imaging 2000; Physics of Medical Imaging, Proceedings of SPIE Vol. 3977 (2000) pp 396–407 (Reference [3]), discloses an example of a computed tomographic system in which the X-ray source and detector (gantry system) are scanned at constant rotational speed. Each X-ray exposure is synchronised with a frame-grabber by hardware trigger pulses for each exposure position. The trigger pulses are evenly distributed over the scanning circle rotated by about 1.25 degrees, and at a frequency of about 30 Hz. The exact position of the scan for each trigger is recorded by way of an optical encoder.

A scan time for 288 projections at a frame rate of 15 frames per second (fps) takes 19.2 seconds and comprises two 144 image scans.

Although image intensifiers are capable of continuous readout, they are limited to about 30 frames/second output. While this may allow continuous rotation of the X-ray source around the object the slowness of the readout results in long scan times (around 17 seconds-20 seconds in dental case). On the other hand, the flat panel semiconductor technology is unable to yield continuous readout during scanning due to their intrinsic high noise and general lack of speed. Thus, flat panel detectors need to operate with discrete exposures.

Drawbacks and disadvantages of the known systems are that the scanning is halted for each exposure position [2], and that frames are read at discrete intervals [3], during a scan. Thus, scanning takes a significant period of time, e.g. around 18 seconds, during which a patient undergoing dental imaging, for example, would have to keep their head still. This is inconvenient and sometimes difficult for the patient, resulting in the likelihood of blurred images due to the patient moving their head.

Particular aspects of the invention are set out in the accompanying independent and dependent claims. Features from dependent claims may be combined with those of the independent claims in any appropriate manner and not merely in the specific combinations enumerated in the claims.

In accordance with a first aspect of the present invention there is provided an imaging system for high energy radiation direct conversion scan imaging. The imaging system includes a high energy radiation source member and a semiconductor high energy radiation direct conversion imaging device arranged around an object position. The imaging device includes a plurality of imaging cells, each imaging cell comprising a detector cell and a readout cell for producing imaging cell output values representative of high energy radiation incident on the detector cells. The source member and/or the imaging device are arranged to move substantially continuously relative to each other for scanning an object at the object position. The readout cells are operable to readout the imaging cell output values at time intervals which substantially correspond to an object image point traversing half the distance of a detector region or cell in the scanning direction.

Viewed from a second aspect, there is provided a method of high energy radiation direct conversion scan imaging using an imaging system including a high energy radiation source member; and a semiconductor high energy radiation direct conversion imaging device including a plurality of image cells, each imaging cell comprising a detector cell and a readout cell for producing imaging cell output values representative of high energy radiation incident on said detector cell; the method comprising: moving said source member and/or said imaging device substantially continuously relative to an object position for scanning an object of said object position; and reading out imaging cell output values at time intervals substantially corresponding to an object image point traversing half the distance of a detector region in the direction of scanning.

Reading out imaging cell output values at time intervals substantially corresponding to an object image point traversing half the distance of a detector region or cell provides a resolution equal to detector region size which at best is equal to image or pixel cell size. Thus, data for region or image pixel cell resolution is possible for the scanning speed.

The readout cells are preferably operable to read out an imaging cell value from each of at least a subset of the plurality of imaging cells during each of said time intervals.

An object image point includes any point within a part of an object to be imaged projected via high energy radiation onto the imaging device. In other words the image point corresponding to the radiation incident on a detection cell, and coming from or through a point in the object to be imaged.

Viewed from a second aspect, the present invention provides an imaging system as aforesaid wherein said source member and/or said imaging device are moveable to image a part of an object in said object position from two or more positions.

The subset of imaging cells corresponds to those cells active for the scan.

The reading out of image cells output values from all the active cells corresponds to the reading of an image frame, and the term frame used hereinafter includes such a definition.

In one embodiment of the present invention, there is provided a system as described above, which in use comprises a high energy radiation source operated to continuously radiate during the scanning process.

Embodiments in accordance with the present invention can advantageously be operated with continuous irradiation of X-rays during a scan without blurring of the final image. Thus, scanning can be achieved in a substantially shorter time, for example 1 to 10 seconds, than is possible with known flat panel or image intensifier techniques which take around 18 seconds to perform a scan. Consequently, for medical applications there is greater comfort for a patient since they only have to keep still for a relatively short period of time, and there is therefore less likelihood of artefacts or blurring in the final image due to patient movement. Furthermore, the X-ray source does not need to be left on for as long as with conventional systems, or rapidly switched on and off, thereby prolonging its life. Additionally, image resolution is only limited by pixel detector size providing the read rate is sufficiently fast, and the scan rate or time to perform a scan is limited only by the readout rate.

Embodiments of the current invention can provide typical readout speeds capable of achieving multi slice tomographic imaging and/or reducing the scan time of 60 frames/second or more, preferably 100 frames/second or more and even more preferably 200 frames/second or more. With embodiments of the current invention frames rates of up to 1000 frames/second or even more are readily achievable without the technology being limited to any specific maximum frame rate.

Additionally, for non-destructive testing (NDT) applications, a faster throughput of devices or articles to be inspected is achievable.

Automatic X-ray Inspection (AXI) systems is one example of NDT and is another very important application for embodiments of the invention. In the electronics industry one of the main production functionalities is the mounting of electronic components and particularly processors, memory chips etc. with the use of ball grid arrays rather than the previously used old fashioned wire bonding. Each chip is mounted on one face of a printed circuit board which carries on a second face an array of conductive metal balls usually based on solder. This printed circuit board is then mounted on a mother printed circuit board. The advantage of using ball grid arrays is that space is saved and the overall mother board architecture is more efficient. However, solder balls may have defects that cause the joints to fail. Such failures include voids, shorts, cracks etc. Using X-rays it is possible to detect and exclude such joints and boards from a final product in real time and on line. The industry and market for assembling such high performance boards is huge, and is growing every year. Today, CCD based systems are most commonly used as X-ray sensors in AXI systems. The X-ray beam is typically electronically guided and the focal spot moves. This is achieved by employing an electron beam that goes through an electronic lens system and scan-hits the X-ray tube target, which can be any suitable target material such as tungsten, molybdenum etc. The resulting X-ray focal spot is consequently moving and the X-ray beam can scan through the object and penetrate the object (PCB) from different directions. Optionally or additionally the PCB moves on a conveyor belt. The CCD sensor is rotated and collects/integrates the X-rays throughout the rotation. Such systems have recently been displayed to the public at industrial exhibitions. The operation results in a tomographic image of the ball grid array of the PCB and the image is a "salami" slice along a given plane that "cuts" through the ball grid array. Flat panels can also be used to achieve the same result. In an embodiment of the current invention a sufficiently high readout speed results in extra amount of image data which can be used to reconstruct other tomographic planes of the ball grid array. This is very important because it increases the throughput of test articles and throughput in this type of business is of the essence. Neither CCD's or flat panels or image intensifiers can achieve this kind of frame readout speed, which for embodiments of the current invention to achieving multi slice tomographic imaging is 60 frames/second or more, preferably 100 frames/second or more and even more preferably 200 frames/second or more. Frames rates of up to 1000 frames/second or even more are readily achievable by embodiments of the invention without the technology being limited to any specific maximum frame rate. A further advantage of frames being output at a very high frame rate is that a pixel in a final digital panoramic image can consist of several image or pixel cell output values from different frames. A final image is constructed of several frames which partly overlap each other. Reconstruction of the image can be done in a computer or in hardware. In the panoramic image, the wanted layer is displayed or manifest as a sharp region in the image and everything else is motion-blurred to a greater or lesser extent depending upon how far from the sharp layer the object is. Typically, in dental imaging, the wanted layer is selected to follow the centre line of teeth. However, different people have different sized skulls and the sharp layer is not always where the doctor or dentist would wish it to be. Appropriate reconstruction of the image using a computer for example, can generate a sharp layer in the desired position.

In the present invention, the frames are stored separately in hardware, or optionally or additionally in computer memory, and therefore there are more possibilities to reconstruct the final image. Optionally or additionally, several images can be created with sharp layers of different depths. From the stored frames, several layers can be produced and viewed on a computer screen. By combining several layers, it is possible to construct a three dimensional image.

By using a digital system, the film cassette is replaced by the imaging device. Unlike film-based systems, the imaging device may be made very narrow, and indeed much narrower than a film cassette. Preferably, the imaging device is made only slightly wider than the X-ray beam. In film systems, a desired projection is achieved by moving the film cassette as the system rotates so that the projection of a desired layer moves across the film during rotation of the system, which requires complex mechanical arrangements for moving the cassette. However, in the digital system the imaging device remains stationary reading out frames at a high speed. High frame readout is necessary in order to prevent or inhibit motion blurring in the direction of rotation. The frames are stored for later processing by hardware and/or computer software. Optionally, the frames can be processed in real time. As new frames are required they are added to a previous image by shifting them in the direction of rotation so that the same objects in the two frames overlap each other. The amount of shift necessary can be calculated from the speed of rotation, the frame rate, the centre of rotation and the position of the desired object layout.

Suitably the source member and/or imaging device are moveable relative to each other to image a part of an object at the object position from two or more positions. Typically the source member and/or imaging device are arranged to rotatably move relative to the object position. Such relative movement provides for a scanning operation of the object, in particular the rotatable movement provides for scanning around an object such as a patient's head for dental panoramic imaging or dental computerised tomographic imaging for example.

Advantageously, the source member and/or imaging device are rotatably moveable about a moveable axis of rotation. Thus, for a fixed object, or object moveable only in a fixed plane, different or desired object planes may be imaged.

In one embodiment particularly suitable for in-line high energy radiation inspection or AXI systems the source member and/or imaging device may be arranged for linear movement relative to the object position. For example, an object to be inspected may be moved along a conveyor belt through an imaging system having a fixed source member and imaging device. Optionally, the source member and/or imaging device may be linearly moveable relative to a line of objects to be inspected. Such an arrangement is particularly suitable for high throughput in-line non-destructive testing (NDT).

The source member may comprise a high energy radiation source. Optionally, the source member may comprise a support suitable for carrying a high energy radiation source. A system providing a support for a high energy radiation source has an advantage in that maintenance and replacement of the radiation source is relatively straightforward, since it can be removed from the imaging system.

The high energy radiation source may comprise a steerable beam high energy radiation source, which provides for a simplified imaging system in which only the imaging device need be moveable relative to the object position. Optionally, the source member may also be moveable even though it comprises a steerable beam source to provide yet a further degree of freedom of movement.

The beam may be electronically steerable, which advantageously simplifies the imaging system since it avoids the use of mechanical arrangements for steering the beam.

In a particular embodiment the imaging device is operable to readout the imaging cell output values at time intervals which correspond to an object image point traversing a part of the detector cell. Thus, the system ensures that there is no blurring of images by way of an object image point being incident on more than one detector cell between reading image cell output values. In a particularly suitable embodiment the time intervals substantially correspond to an object image point traversing half a detector cell.

In a particular embodiment the readout cell is operable to readout the imaging cell output values during or whilst the object image point traverses the detector region or cell. Suitably, the imaging cell output values may be read substantially continuously during the traversing of the object image point over the detector region or cell.

In one embodiment the readout cells are operable to readout imaging cell output values after the object image point has traversed the detector region or cell, which allows for a maximum amount of incident radiation on a detector cell prior to reading the output value.

In a particular embodiment, the imaging device is arranged such that cell output values may be read for more than one detector cell on each readout cycle. Typically, more than one adjacent detector cells are logically grouped together, and the cell output values for the group of detector cells is read in one readout cycle. Advantageously, such a configuration allows for a reduction in the resolution of the image, but with a corresponding increase in image acquisition speed.

Evidently, for such an arrangement in which cell output values for more than one detector cell are read for each readout cycle an object image point may traverse more than one detector cell. That is to say, the object image point would traverse, in the direction of scanning, across substantially all the detector cells for which the cell output values will be read together in a single readout cycle. Those detector cells for which the cell output values are read together form a detector region.

Suitably, the readout cells are operable to readout the imaging cell output values at a rate of substantially 5 MHz or more, preferably 10 MHz or more and yet more preferably a rate of 20 MHz or more.

According to one aspect of the invention the imaging device is operable to readout the imaging cell output values at a frame rate of 60 frames/second or more preferable 100 frames/second or more and even more preferably 200 frames/second or more. Frame rates of 1000 frames/second or more are readily possible. Typically, the imaging system comprises a plurality of imaging devices, thereby providing a larger imaging area than achievable utilising a single imaging device. For a particularly advantageous embodiment two or more imaging devices may be coupled together for reading out imaging cell output values from more than one device into a readout channel. Thus, the number of readout channels, and corresponding interface circuitry, are reduced thereby reducing the complexity of the imaging system.

Typically the imaging system is interfaceable to data acquisition and control apparatus for receiving and storing imaging cell output values. In a preferred embodiment, the data acquisition and control apparatus comprises a personal computer, including a display screen for displaying images received from the imaging system.

The imaging device of the imaging system includes readout cells comprising high speed integrated circuitry. Preferably the high speed integrated circuitry is CMOS circuitry, which has the added advantage of being low power and having low heat dissipation.

Other technologies that can be used to produce high speed integrated circuitry include Double Poly MOS, NMOS, JFET, p2CMOS, XMOS, GaAs integrated circuit processes, ECL, TTL, Bipolar Linear, BiCMOS, EEPROM/FLASH process, SALICIDE process, Optoelectronics, Complimentary Bipolar DLM2, Copper Fine Line, and BCD (Bipolar/CMOS/DMOS), for example.

Illustrative embodiments of the invention are described hereinafter, by way of example only, with reference to the accompanying drawings, in which.

Figure 8:
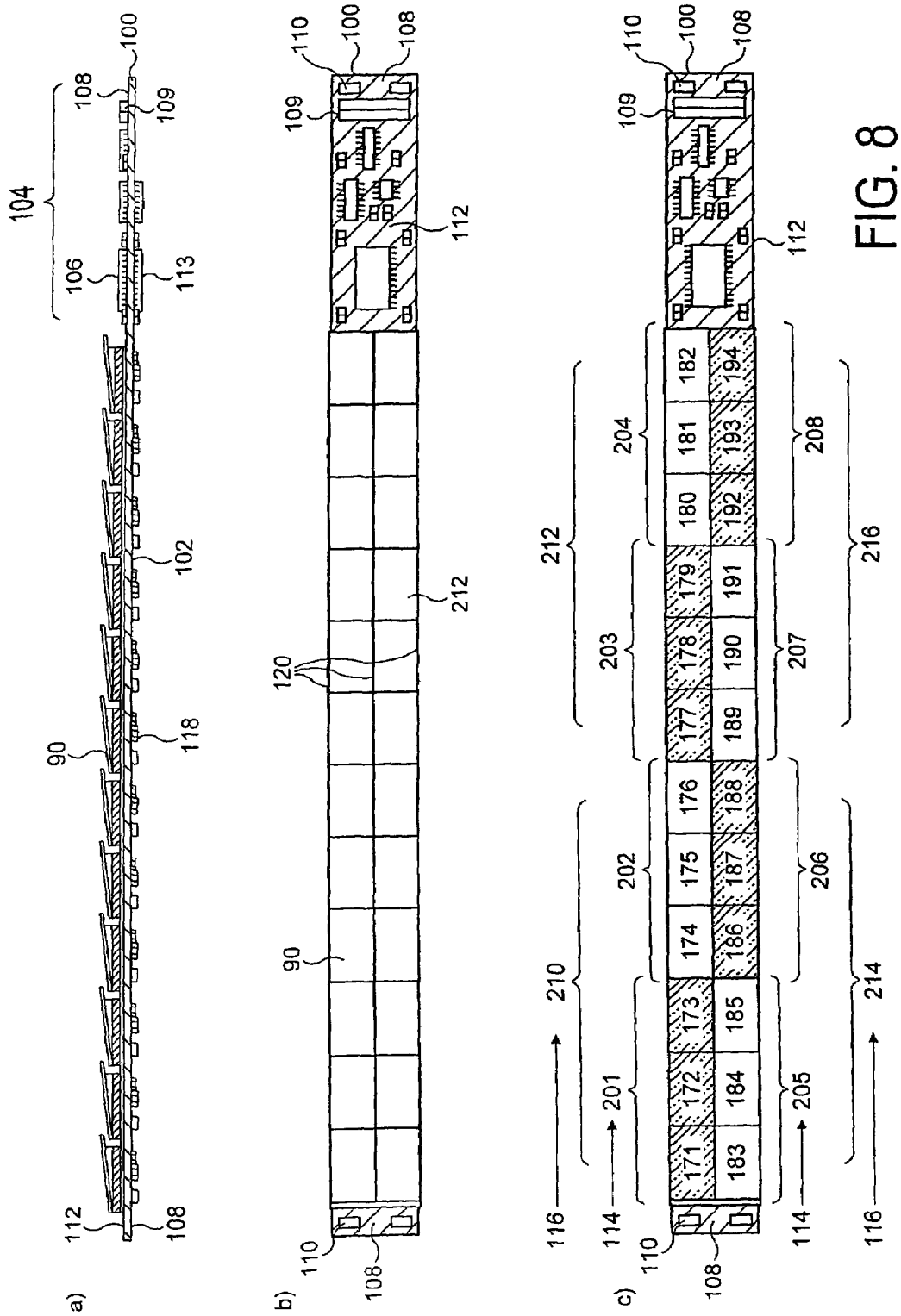
Figure 9:
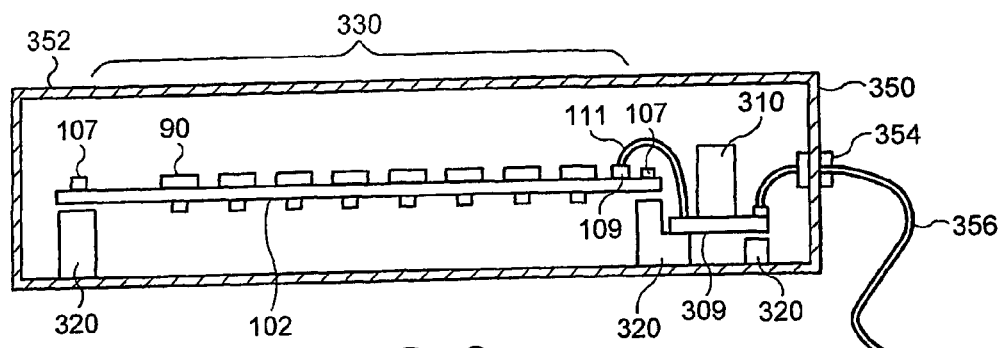

FIG. 8 comprises schematic side, plan and functional diagrams of an example of an imaging module according to an embodiment of the invention;

FIG. 9 is another cross-sectional side view of a cassette; and

Figure 10:
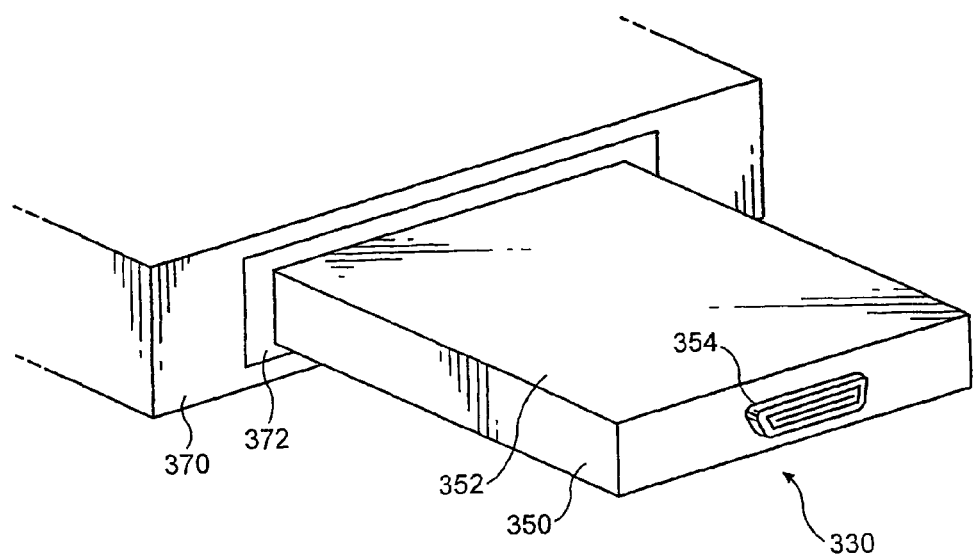
Figures 11, 12:
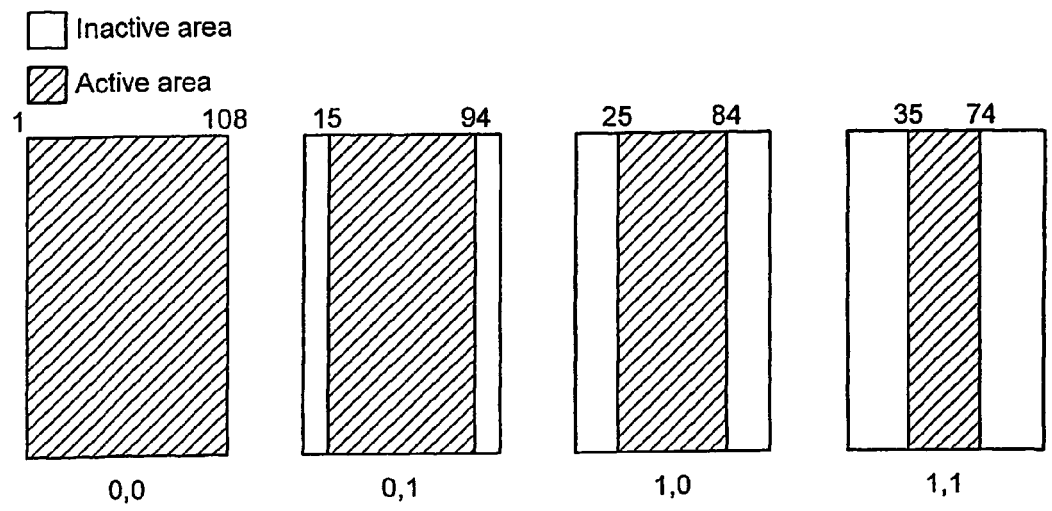
Figure 13:
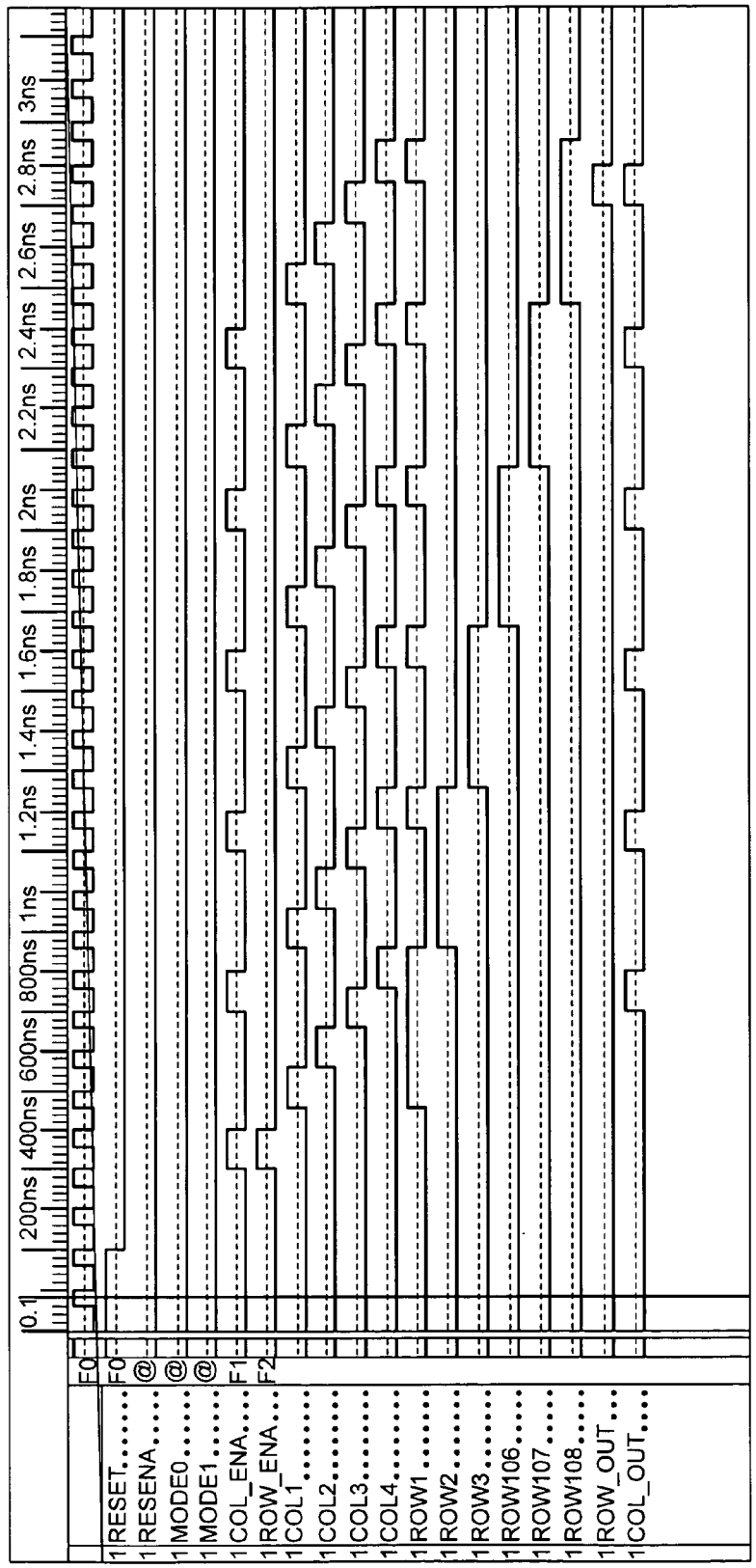
Figure 14:
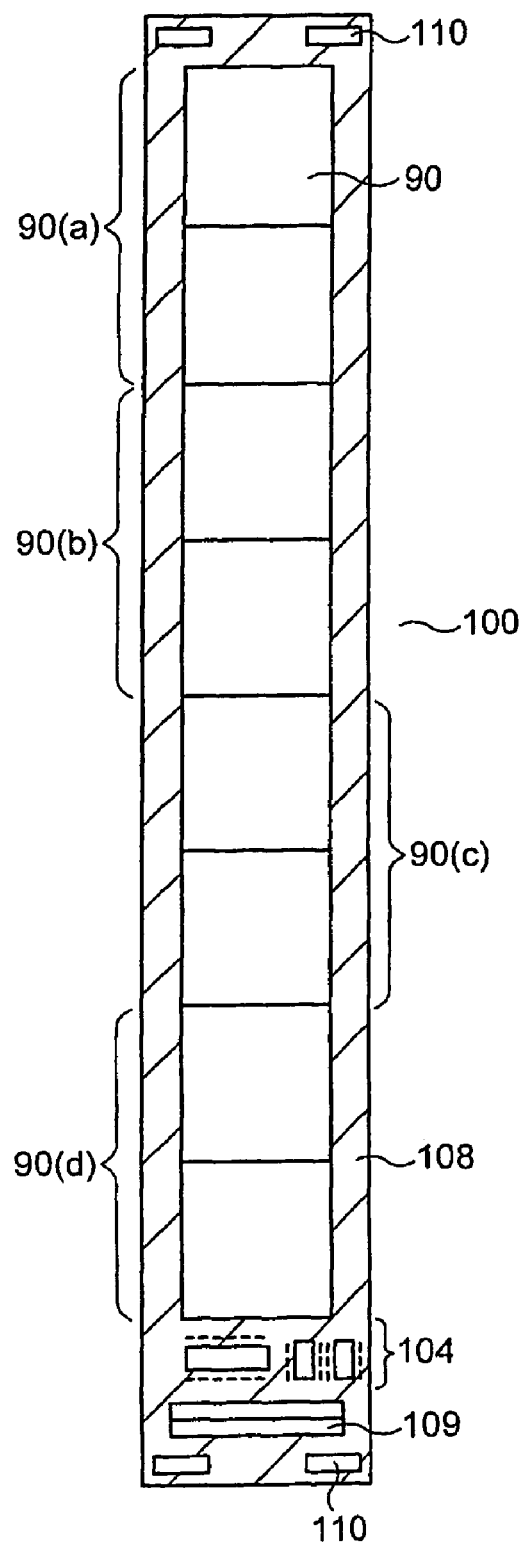
Figure 15:
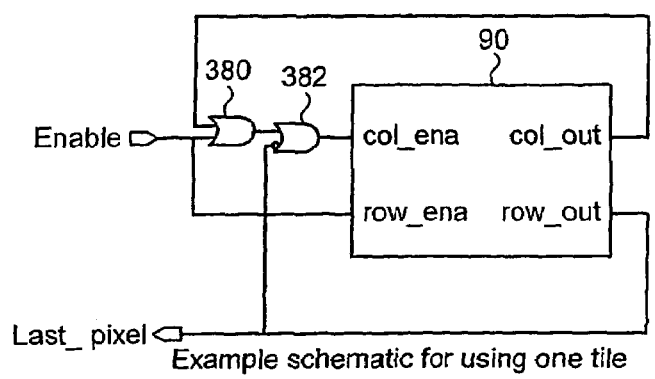
Figure 16:
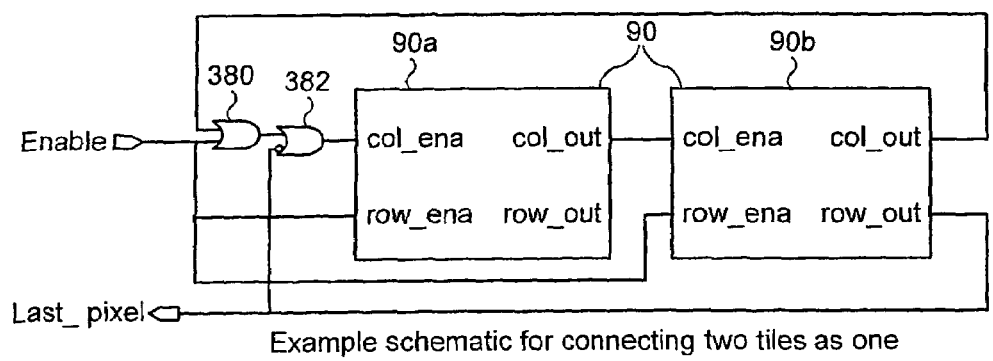
Figure 17:
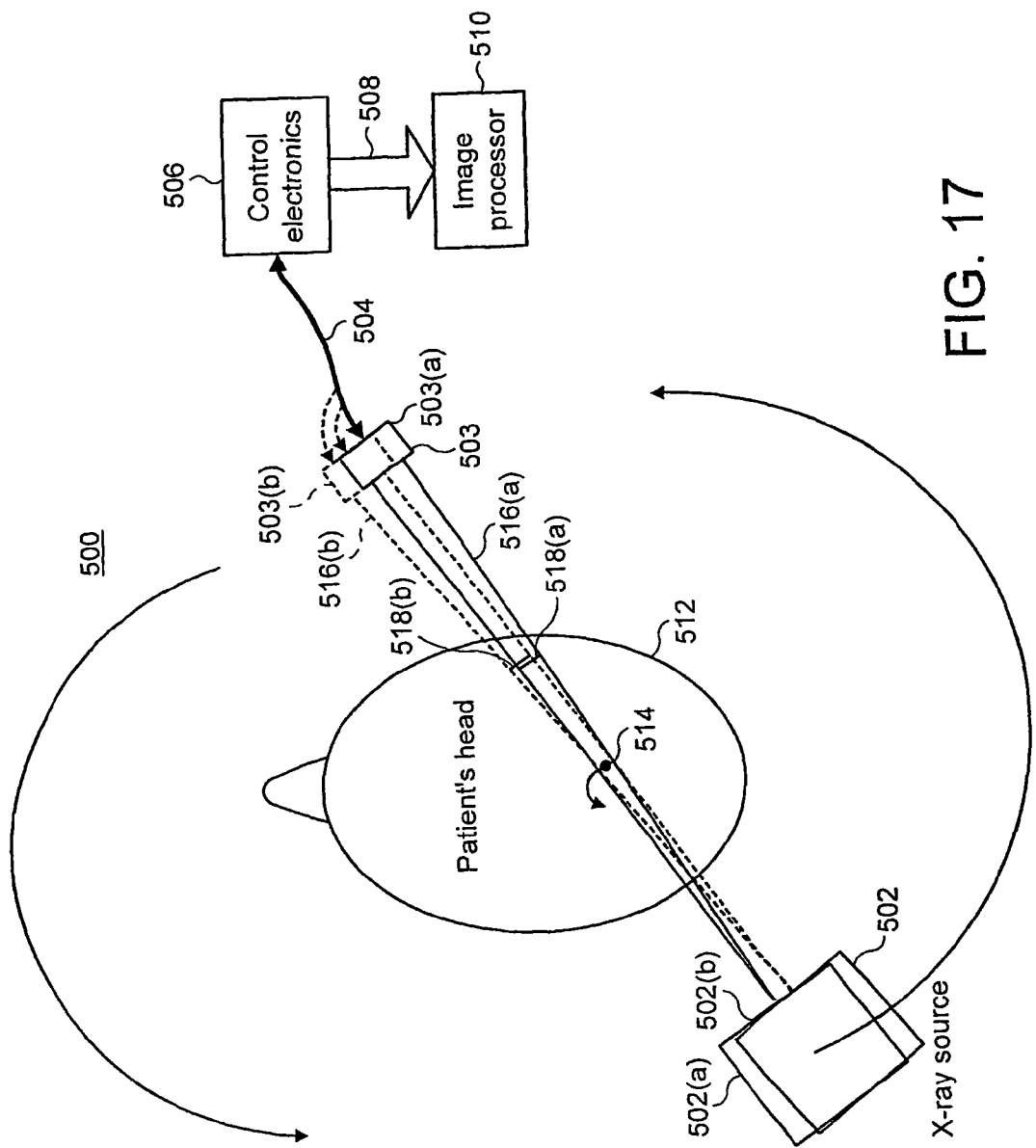
Figure 18:
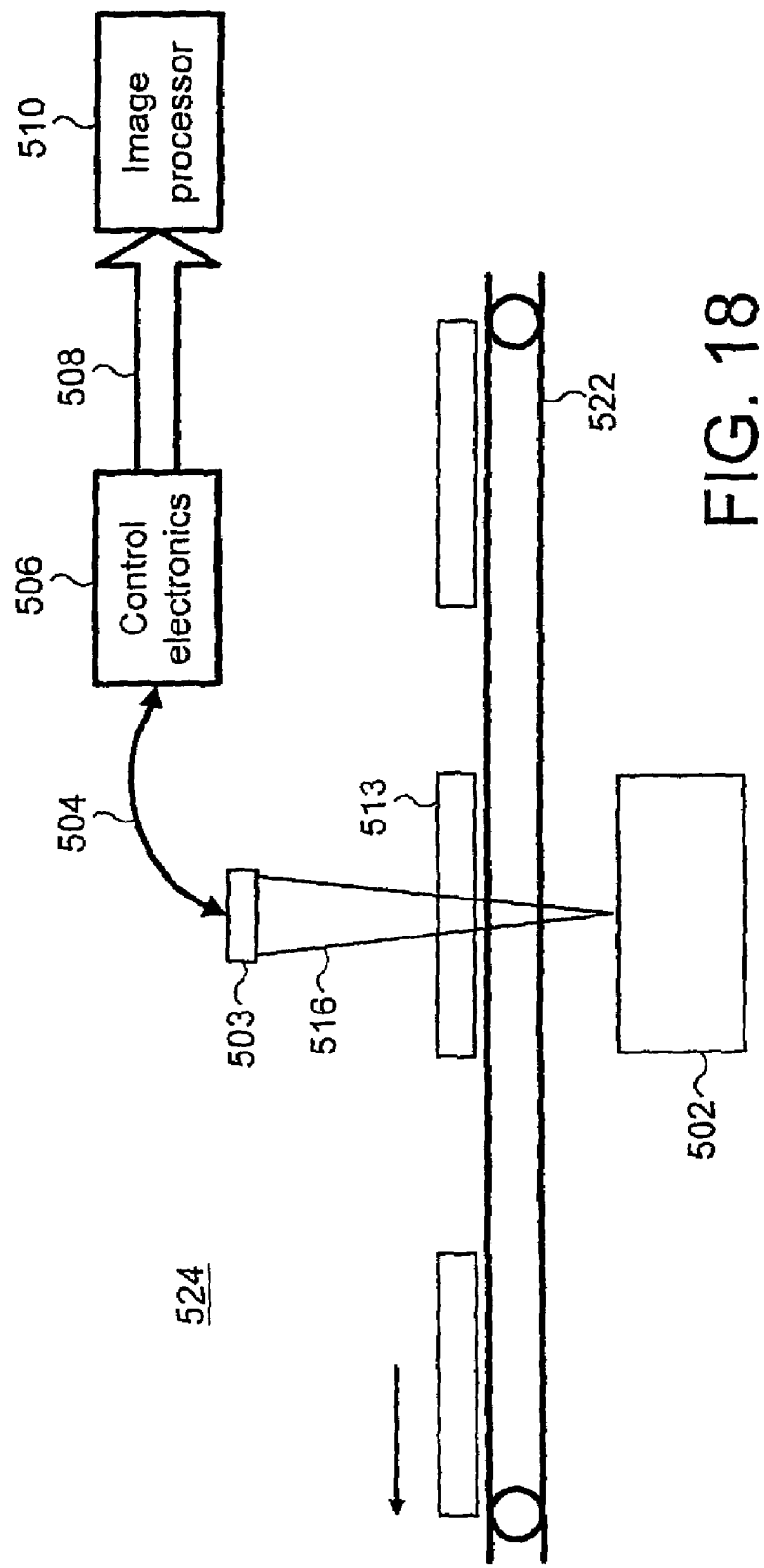

FIG. 10 is a schematic external view of a cassette;

FIG. 11 illustrates operational modes of an imaging device for an embodiment in accordance with the invention;

FIG. 12 illustrates a table;

FIG. 13 illustrates a timing diagram;

FIG. 14 illustrates an embodiment of the invention;

FIG. 15 illustrates logic circuitry arranged to readout one device at a time;

FIG. 16 illustrates logic circuitry arranged to readout two devices in series;

FIG. 17 schematically illustrates a panoramic imaging system using one embodiment of the invention; and FIG. 18 schematically illustrates an automated X-ray testing system using an embodiment of the invention.

Figure 2:
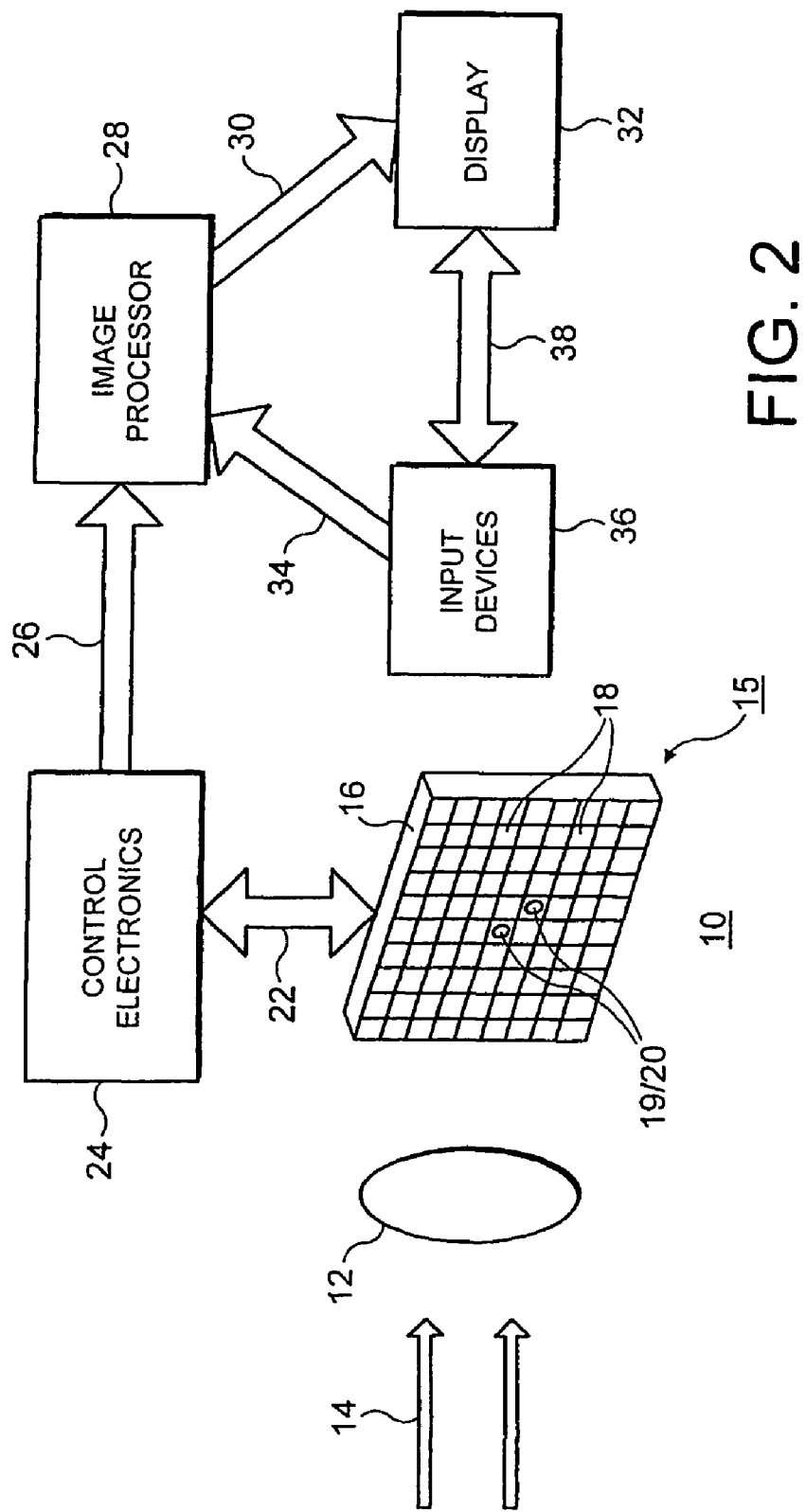
FIG. 2 is a schematic representation of an imaging system.

FIG. 2 is a schematic representation of an example of an imaging system 10 as described in the Applicant's International application WO 95/33332 for radiation imaging of an object 12 subjected to radiation 14. The radiation may, for example, be X-ray radiation and the object 12 may, for example, be a part of a human body. The imaging device comprises an imaging array 15 including at least one Active-pixel Semiconductor Imaging Devices (ASID) 16. Although only one ASID 16 is shown schematically in FIG. 2, the imaging array will typically include a plurality of imaging devices 16. Each imaging device 16 provides a plurality of image, or pixel cells 18. Each imaging device directly detects high energy incident radiation such as X-rays, γ-rays, β-rays or χ-rays and accumulates at each pixel cell, by means of an individually accessible or addressable, active, dynamic image cell circuit on or adjacent to a corresponding image detector cell, values representative of the radiation incident at that image cell. The phrase "individually accessible or addressable" is intended to encompass pixels which are independently addressable of each other (e.g. in random or sequential order).

The imaging device 16 can be configured as a single semiconductor substrate (e.g., silicon) with each image or pixel cell comprising an image detector cell 19 and an active image cell circuit 20, or alternatively on two substrates, one with an array of image detector cells 19 and one with an array of active image cell circuits 20, the substrates being mechanically connected to each other by, for example, microbumps (bump-bonds).

Figure 3:
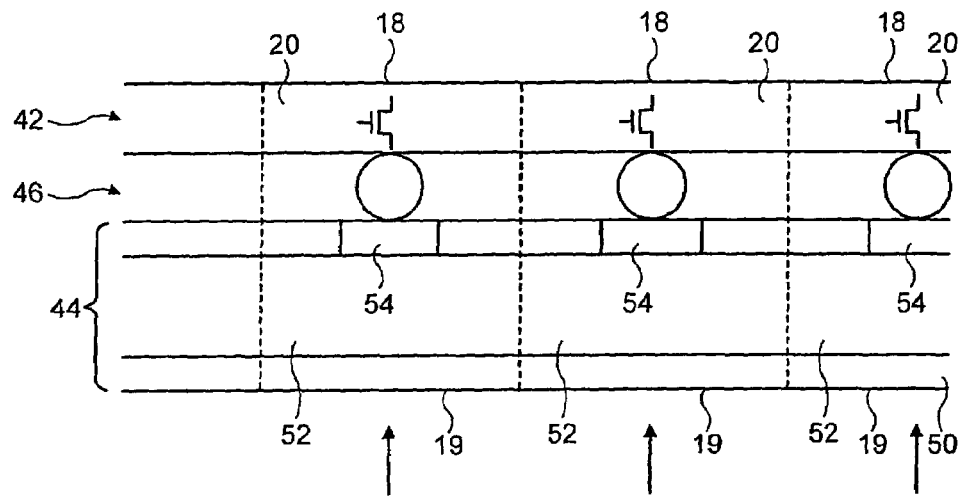
FIG. 3 is a schematic partial cross-section of an imaging device sensor.

FIG. 3 is a schematic partial cross-sectional representation of a two-substrate imaging device or sensor showing the connection of the substrates. Individual detector cells 19 of an image detector substrate 44 are connected to corresponding cell circuits 20 of a readout substrate 42 by means of microbumps 46. The image detector substrate 44 is made of, for example, Si, CdZnTe, CdTe, $HgI_2$, GAs, Ge or TIBr. High resistivity Si is preferred as the detector material for maximum image sharpness whereas CdTe is preferred in applications demanding high quantum efficiency and low radiation dose. The cell circuits 20 are schematically represented within the substrate 42 by means of the symbol of a FET.

The detector substrate 44 is provided with a continuous electrode 50 on the side of the substrate 44 which is exposed to incident radiation. In FIG. 3, therefore, the incident radiation is assumed to arrive in an upwards direction. On the rear surface of the detector substrate 44, a plurality of detector cell electrodes 54 are provided. It is the array of detector cell electrodes 54 which effectively defines the individual image detector cells 19 within the detector substrate 44. A bias voltage is applied to the continuous electrode 50 and image cell detection zones 52 are defined between the continuous electrode 50 and the respective detector cell electrodes 54. Each of the detector cell electrodes is electrically and mechanically coupled to a respective cell circuit 20 by a respective microbump 46. It will be appreciated that the representation in FIG. 3 is highly schematic, and not to scale.

When a photon is photo-absorbed at a detector cell 19 creating an electric charge or when charged radiation ionizes the detection zone 52 of the detector substrate 44 at a detector cell 19, an electric pulse flows from the detector substrate detection zone 52 to the cell circuit 20 for that image cell 18.

A value associated with the electric pulse is then accumulated in an active circuit element, either directly as a charge value or as an equivalent voltage or current value such that new charge created from subsequent incoming radiation is added continuously. Examples of possible accumulating devices are an integrated capacitor or the gate of an integrated transistor. The charge accumulation process in a cell circuit 20 continues until control signals are issued from control electronics 24 to start a process of reading out information by addressing each cell circuit 20, effectively in a random or individual access manner. During readout of the accumulated charge values, charge continues to be accumulated. Cell circuits 20 may selectively be reset after readout to discharge the charge accumulation circuit elements, and only then are image cells inactive for a very short time with practically no dead time.

Thus, the cell circuits 20 are provided for each image cell 18 to accumulate charge created in the detector cell when, for example, a photon or a charged particle of radiation is incident on the detection zone of that detector cell 19. An active cell circuit 20 and the detector cell 19 can be of the order of a few tens of microns in size (e.g., 10–50 μm).

A schematic representation of an example of a cell circuit is described with reference to FIG. 4. This example of a cell circuit uses field effect transistors (FETs) arranged as a cascode connected amplifier. FET M11A 70, and in particular the gate thereof, forms charge accumulation circuitry. FET M11B 72 forms readout circuitry. FET M11C 77 forms reset circuitry. VBIAS 60 is a bias voltage input across the depletion zone forming a detector cell 19 of the image cell. The detector cell 19 is represented by a diode symbol D11. In the cell circuit itself, SIGOUT 62 is an analog signal output and VANA 64 an analog power supply input. RES-R-1 66 is a reset input and ENA-R-1 68 is an enable input for the cell circuit.

Charge generated in the detector cell 19 in response to incident radiation is automatically accumulated in the gate of a transistor M11A 70 when both the RES-R-1 66 and ENA-R-1 68 inputs are low. To read the image cell, ENA-R-1 68 is taken to a high state, which allows current to flow from the transistor M11A 70 through the transistor M11B 72 to SIGOUT 62. The cell circuit is reset by taking RES-R-1 66 to high, whereupon after RES-R-1 66 has been at high for merely a few microseconds, any accumulated charge will have been removed from the gate of the transistor M11A 70. Immediately after RES-R-1 66 goes to a low level, charge can begin to accumulate at the gate of the transistor M11A 70. If no reset pulse is supplied to the reset input RES-R-1 66, then it is to be noted that a reading operation when the enable input ENA-R-1 68 goes high does not destroy the charge but instead merely causes a current flow directly proportional to the accumulated charge. This allows multiple readings without resetting.

Figure 4:
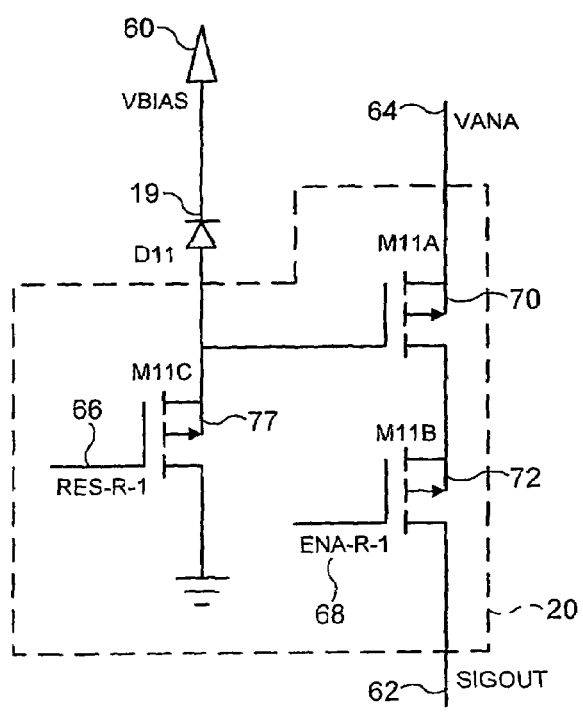
FIG. 4 is a schematic representation of an image cell circuit.

In the example shown in FIG. 4, charge accumulation ability can be maximised by arranging that the gate capacitance of a charge accumulation transistor M11A 70 forms substantially (say greater than 60% and preferably 90% of)

the input node capacitance (total capacitance) of the detector cell 19, the charge accumulation circuitry 70, the readout circuitry M11A 72 and reset circuitry 77 of FIG. 3 and minimizing the parasitic or unwanted capacitance of all other circuit (and detector) components. For a 35 μm by 35 μm cell circuit, for example, the M11A 70 capacitance can be 2 pF and the FET gate voltage dynamic range can be at least 2 Volts. This corresponds to about 25,000,000 electrons in storage capacity.

Returning to FIG. 2, the control electronics 24 includes processing and control circuitry, which is connected to the cell circuits 18 on the semiconductor substrate as represented schematically by the two-way arrow 22. The control electronics 24 enable the cell circuits 20 associated with individual image cells 18 to be addressed (e.g., scanned) for reading out charge accumulated in the cell circuits 20 at the individual image cells 18. The charge readout is supplied to Analog to Digital Converters (ADCs) for digitisation and Data Reduction Processors (DRPs) for processing the binary signal. A readout corresponding to all the image cells is an image frame, and the control electronics may comprise a frame grabber.

Figure 5:
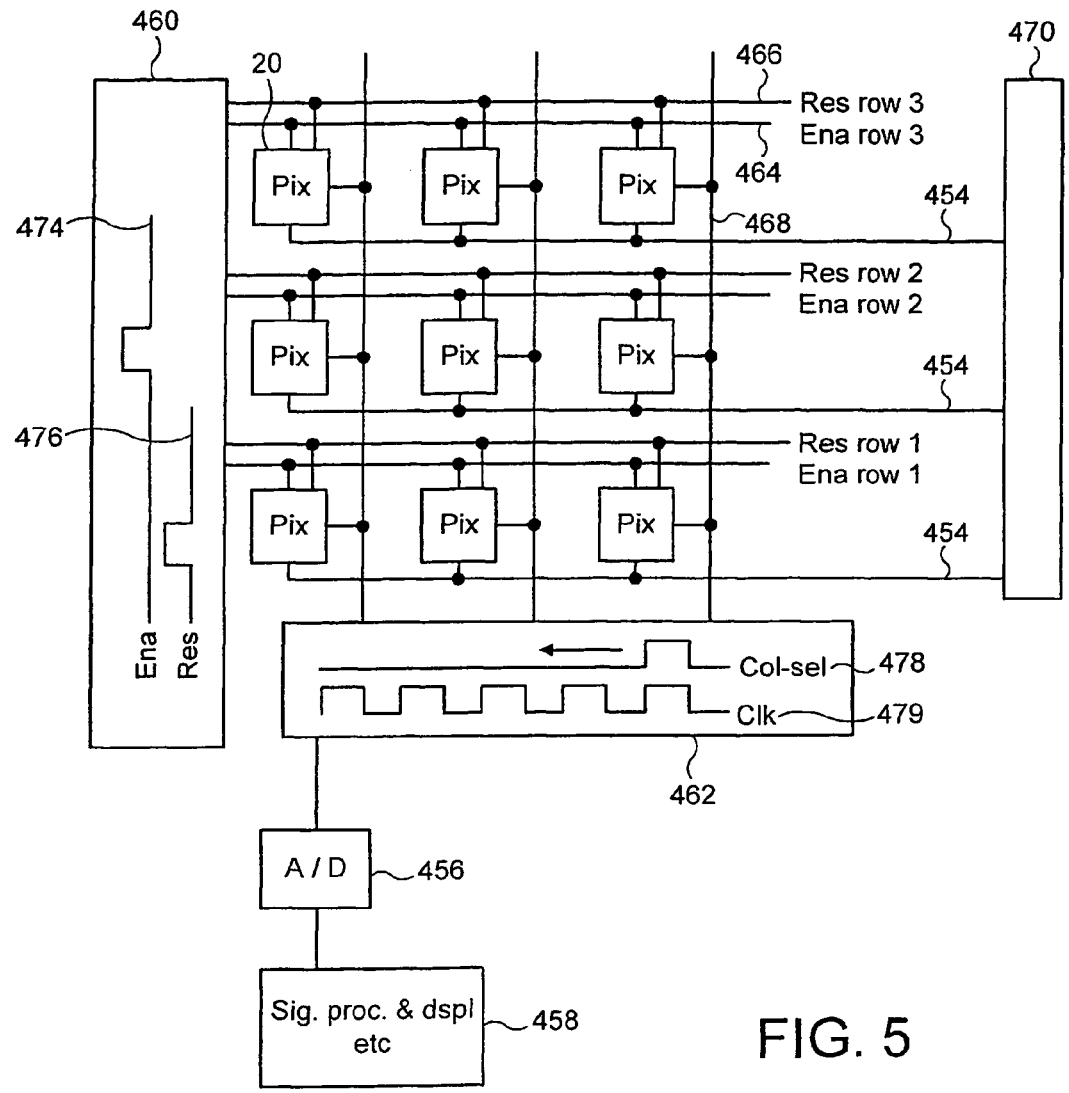
FIG. 5 is a schematic diagram of part of an imaging array and control electronics for an imaging device in accordance with an embodiment of the invention.

FIG. 5 is a schematic representation of one possible configuration of the control electronics 24 of FIG. 2 and the relationship of the control electronics 24 to an m×n matrix of the active circuits 20 of the pixel cells 18. For ease of illustration an array of 9 pixel cells is illustrated in FIG. 5 and only some of the signal lines which make up the path 22 in FIG. 2 are shown. It will be appreciated that an imaging device in accordance with the invention will normally include a significantly larger number of pixel cells than are shown in FIG. 5. The row select logic 460 controls the row readout 474(ENA) and the row reset 476(RES) and the column logic 462 enables (COL-SEL) 478 for the readout accumulated charge values from each pixel circuit 20 in response to a clock signal 479.

The control electronics 24 include row select logic circuits 460, column address logic circuits 462, power supply circuits 470, Analogue to Digital Converter (ADC) 456 and the signal processing circuits 458. Preferably some, if not all, of the control electronics 24 is implemented on the substrate at the periphery of the image array formed by the array of pixel cells 18.

The power supply circuits 470 provide power for the individual active circuits 20 on the pixel cells 18 via lines 454 (shown schematically in FIG. 5) and can additionally be arranged to supply the biasing voltage via lines (not shown) for the electrodes defining the pixel cells.

The row select logic 460 provides signals via row enable and reset lines 464 and 466, respectively (also shown schematically in FIG. 5), for selecting columns for the reading and resetting, respectively of the individual active circuits 20 of the pixel cells 18. The row select 464 and row reset 466 lines are connected to the enable input ENA-R-1 and the reset input RES-R-1 66, respectively of each of the pixel circuits of the row. Also shown in the row select logic 460 are row enable 474 and row reset 476 signals for scanning successive rows. It can be seen that the reset pulse 476 follows the row enable pulse 474 to cause resetting of the active circuits after reading.

The column select logic 462 effectively comprises a multiplexer for selecting signals output via the column lines 468 (also shown schematically in FIG. 5), each column being connected to the SIGOUT output 62 of each pixel circuit 20 in that column. The COL-SEL signal 478 represented in the column select logic 462 thus selects columns for reading the individual active circuits 20 of the pixel cells 18 currently selected by the row enable pulses 474. In the embodiment shown the column select pulse is clocked for successive column positions in response to the clock CLK 479 during one row enable period, so that the accumulated charge value of a respective active pixel circuit on the row currently selected is clocked out at each clock pulse before the row select pulse proceeds to the next row. Each active pixel circuits of the row just read is then reset simultaneously by the row reset pulse 476.

The connections shown in FIG. 5 are readily realisable using conventional double metallisation technology. Although, as described with reference to FIG. 5, the pixels are readout sequentially in a predetermined order, it will be appreciated that the pixels are in effect accessed in a random access or individually accessible manner by means of separate row and column enable signals. It will be appreciated also that the scanning direction could be reversed (rows to columns) or indeed individual pixels could be accessed in a totally random order by suitable row and column enable signals. It will also be appreciated that the degree of sequential or parallel processing can easily be modified to match the needs of each application. For example all rows can be set simultaneously at an enable high state so that the column select clock will output in parallel all rows, thereby increasing the readout rate. The resetting of rows need not match the readout rate. After multiple readings each row may be reset at a lower rate than the readout rate. It will be appreciated that the designation of rows and columns is arbitrary and can be reversed.

Figure 6:
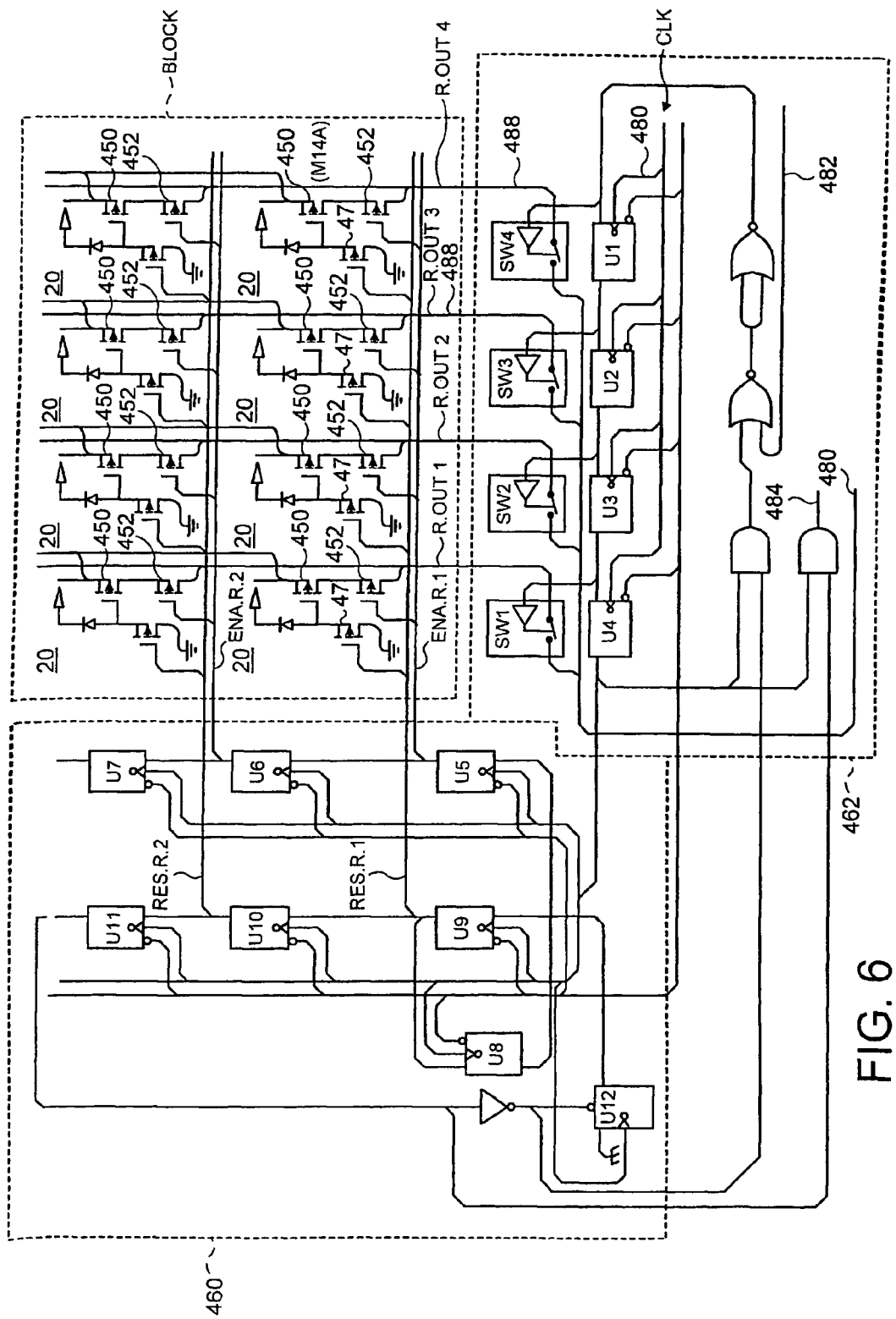
FIG. 6 is a schematic circuit diagram of part of an imaging array and control electronics for an imaging device with blocks of pixel cells of an imaging device in accordance with an embodiment of the invention.

To cover a very large imaging surface in an effective way, the pixel cells are preferably grouped in blocks of m×n pixels with the pixels within a block being readout and reset sequentially in rows. FIG. 6 is a schematic diagram showing a block of two rows by four columns of pixel circuits 20. The pixel circuits accumulate charge on the gates of the transistors MijA, where i=1,2 and j=1,2,3,4. In order to keep the transistors at a low potential, each gate is grounded after reading. Readout is initiated by applying a clock-pulse train to the CLK input 480, and a one clock period high (read bit) to an RB-IN input 482.

During the first clock period the RB-IN input 482 enables the switch SW4, which connects the analogue output line 468 for the fourth column to the analogue output ROUT 488. Thus, when the row enable input ENA-R-1 for the first row is high, which opens the switch transistors M14A52 of the first row, during this first clock period, a signal current representative of any charge stored on the gate of the transistor M14A 450 of the pixel circuit 20(1,4) flows through that transistor and via the switch SW4 to the analogue output ROUT 490.

By the next clock period of the clock CLK, the RB-IN input must be down. The high state, originally at the input of a flip-flop U1 is clocked by the clock train CLK to the input of a flip-flop U2 and switch SW3 which then connects the analogue output line 468 for the third column to the analogue output ROUT 488 so that a signal current representative of any charge stored on the gate of the transistor M13A 450 of the pixel circuit 20(1,3) can flow through that transistor and via the switch SW3 to the analogue output ROUT 490 Because the SW4 is now low (down) the analogue output line 488 for the fourth column is disconnected. The read bit thus ripples through the switches SW4–SW1 and flip-flops U1–U4 for successive clock pulses of the clock CLK. The column enable flip-flops U1–U4 form a first shift register.

When the read bit is clocked out of the flip-flop U4 it is clocked back to the flip-flop U1. It is also clocked to the clock inputs of row-enable logic U5–U7 and row reset logic U9–U11. Each time these receive a clock input from the output of flip-flop U4 they advance a read bit and a reset bit, respectively, the reset bit moving one step behind the read bit. The row enable logic flip flops U5–U7 form a second shift register and the row reset flip flops U9–U11 a third shift register.

In this way, each time a row is readout, the read bit is moved up one row. Similarly the reset bit is moved up one row, but one row behind the read bit. When the reset bit is readout of the last flip-flop U11, it is supplied to the read bit out RBO output 484 and a new read cycle can be initiated. The time between successive read operations should be sufficiently short to keep the gates of the transistors MijA with relatively small potential differences, preferably potential differences below 2V from the reset potential (or potential of zero charge accumulation).

Returning to FIG. 2, the control electronics 24 is further interfaced via a path represented schematically by the arrow 26 to an image processor 28. The image processor 28 includes data storage, e.g. a frame store, in which it stores the digital value representative of the charge read from each image cell along with the position of the image cell 18 concerned. For each image cell 18, each charge value read from the image cell is added to the charge value already stored for that image cell so that a charge value is accumulated. As a result, each image can be stored as a representation of a two-dimensional array of pixel values which can be stored, for example, in a database.

The image processor 28 can access the stored image data in the database to select a given image (all the array) or a part of the image (a sub-sample of the image array). The image processor 28 reads the values stored for the selected image positions and causes a representation of the data to be displayed on a display 32 via a path represented schematically by the arrow 30. The data can of course be printed rather than, or in addition to being displayed and can be subjected to further processing operations. For example, background and noise can be subtracted as a constant from each pixel charge value. This pedestal and/or background subtraction is possible if prior to image taking an "empty" image is acquired. For each pixel a background value is deduced and can be subtracted accordingly.

User input devices 36 connected via paths represented schematically by the arrow 34 and possibly interacting with the display 32 as represented schematically by the double arrow 38 can be used to control the operation of the imaging system. The user input devices 36 can include, for example a keyboard, a mouse, etc. In an embodiment of the present invention the image processor 28, display 32 and input device 36 are all components of a desktop personal computer (PC) system, laptop or notebook computer.

For an embodiment utilising a personal computer, laptop or notebook computer system the interface from the control electronics 24 may be implemented by a Universal Serial Bus (USB) port located on the personal computer system, laptop or notebook computer system comprising the image processor 28. The advantage of using a USB port is that it does not require specially designed circuitry inside the computer, unlike Personal Computer Interface (PC) and Interface Serial Adapter (ISA) buses. Thus, once appropriate software has been installed into the computer system a peripheral need simply be plugged into the USB port. USB V1 only has a maximum bandwidth of 12 Mbps, which is 1.5 MBps. This may restrict the rate at which data may be received from the control electronics 24, and hence the frame rate. However, a second generation USB V2 port is available, which has a maximum bandwidth of 500 Mbps (60 MBps). For high frame rate and image acquisition, it is therefore preferable to use a USB V2 port.

In the Applicant's co-pending UK Patent application GB 9614620.4, an approach is described for providing continuous coverage while, at the same time, preserving the option to replace individual detectors non-destructively. Specifically, this approach applies to hybrid imaging devices comprising a semiconductor substrate 44, bump-bonded to an ASIC CMOS crystalline silicon readout chip 42 as described in the Applicant's International patent application WO 95/33332.

Figure 1:
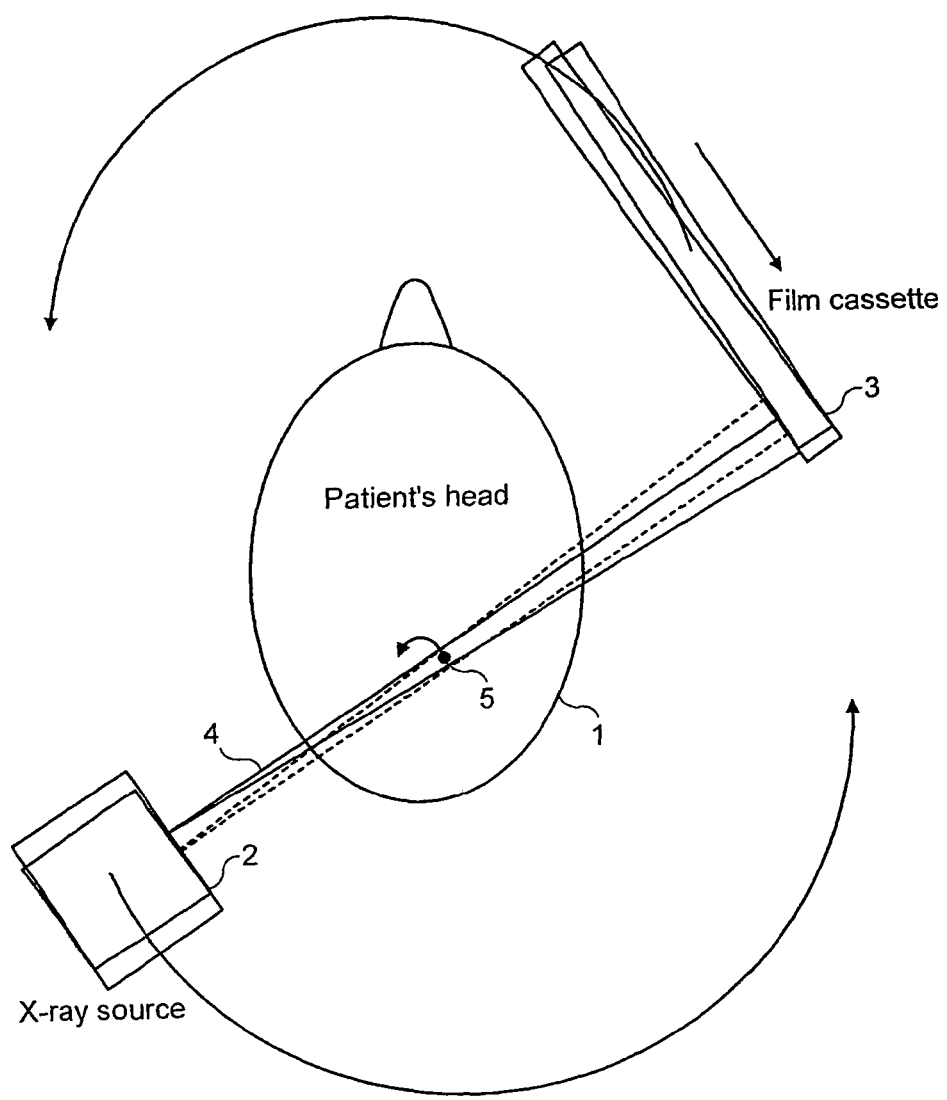
FIG. 1 is a schematic representation of an arrangement for dental panoramic imaging.
Figure 7:
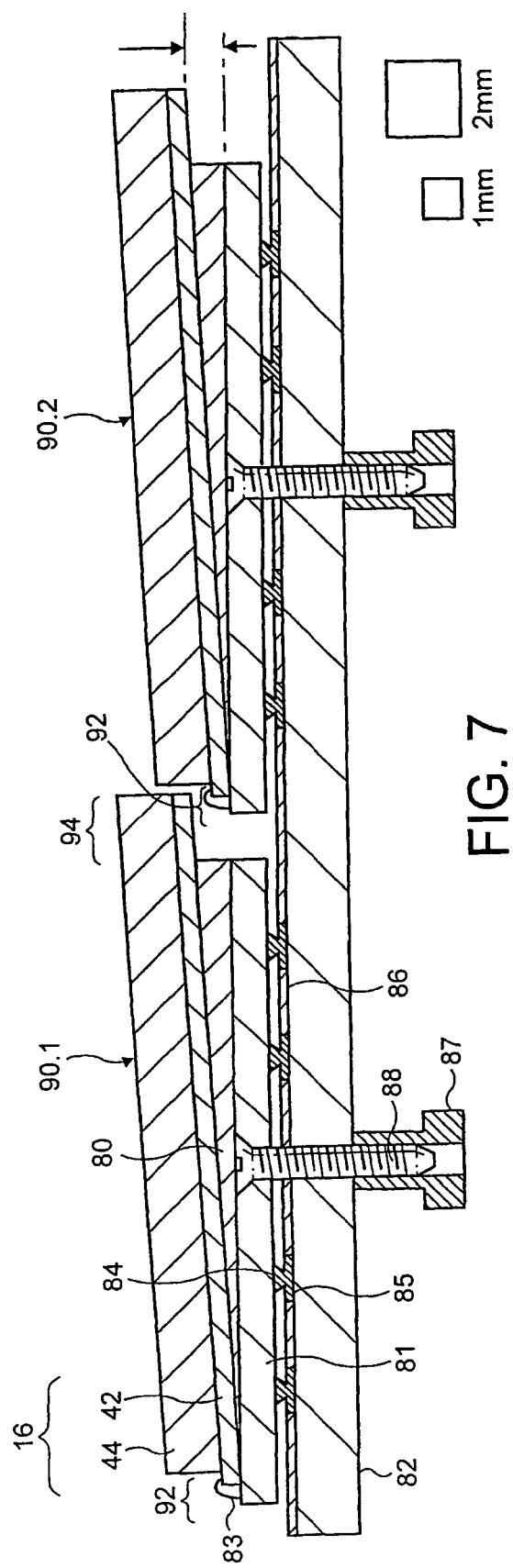
FIG. 7 is a schematic representation of a proposal for an imaging tile.

FIG. 7 of the accompanying drawings corresponds to FIG. 3B of GB 9614620.4. Here the imaging device 16 comprising the bump-bonded detector-readout structure 44/42 described above with reference to FIGS. 1–3 is mounted on a Printed Circuit Board (PCB) mount 81 to form an imaging device called a tile 90. The detector-readout structure 44/42 is tilted with respect to the PCB 81 by means of a wedge 80 or an equivalent structure. In this manner, an active region 94 of a tile (say 90.1) covers an inactive region 92 of a subsequent tile (i.e. the adjacent tile 90.2). A region 92 of each tile is reserved for wire connections 83 between the PCB 81 and the readout substrate 42. Electrical contact between the master support 82 and the PCB 81 is achieved by means through the connection of conductive bumps, or balls, 84 and conductive rings or pads 85. The rings 85 are located at desired positions by means of holes in an insulating layer 86. Below the rings 85 are conductive contacts. The tile 90 is mounted on the master support 82 by means of a screw 88 which projects from the tile mount PCB 81 and a nut 87. Alternatively, other removable fastening means such as zero insertion force connectors, clips, vacuum, etc., can be used removable to secure the tiles on the support.

Image continuity along the direction perpendicular to the plane of FIG. 7 requires a detector active up to the two edges along this direction. The Applicant's co-pending UK patent application GB 9703323.7 proposes a solution to this whereby the detector substrate 44 extends over the readout substrate 42 on all three sides except the side, or region, 92.

The Applicant's British patent application publication number GB 2 332 608A describes imaging modules which are suitable for mounting singly or in plural in an imaging cassette. The imaging cassette may be configured as a replacement for a conventional X-ray film cassette, and comprise a collection of one or more imaging modules, each module comprising one or more imaging tiles mounted thereon.

Configuring a large area imaging plane by way of a plurality of smaller area imaging modules advantageously provides for ease of assembly and replacement compared to a large area imaging plane comprising a plurality of imaging devices mounted on a single large area substrate.

An example of an imaging module is illustrated in FIG. 8, in which is illustrated a schematic side view (a), plan view (b) and functional diagram (c).

FIGS. 8a and 8b depict an example implementation of an imaging module. The example of a module 100 comprises 24 imaging tiles 90 mounted on a multilayer printed circuit board 102. The tiles 90 are arranged in a two dimensional mosaic of two rows and twelve columns on the upper surface, as seen in FIG. 8a, of the module board 102. A region 104 of the module 100 is reserved on the module board 102 for electronic components 106 such as analog electronics, multiplexers, preamplifiers, analog to digital converters, etc., as required for a particular application. Arrangements, for example apertures or openings 110 at the extreme ends 108 of the module board 102, are provided for receiving screws or other fastenings (not shown in FIG. 8) for mounting the module 100 on a cassette support (not shown in FIG. 8). Separate electrical connections arrangements such as cable connectors 109, edge connectors, ribbon cables, etc, can be provided. Alternatively, the module board 102 could be provided with combined mechanical and electrical connector arrangements, for example zero insertion force connector(s), other pin and/or socket connector arrangements etc., which serve to removably locate the board mechanically and provide electrical connections. An insulating material 112 layer separates the tiles 90 from module board 102. The insulating layer 112 is preferably no more than 1 mm thick. Holes 85 (see FIG. 7) are provided, for example by engraving, in the insulating layer 112 for locating conductive rubber pads or rings or other electrically conductive elements, preferably resilient conductive elements, by means of which bump-shaped contacts on the tile 90 can be electrically (power) and electronically (signals) connected to contacts and conductive paths on and in the module board 102. Where conductive rubber pads are used, the rubber thickness is preferably less than under 0.5 mm.

Analog electronic components 113, such as switches, capacitors, coils etc, are preferably placed on the lower surface, as shown in FIG. 8a, of the module board. These components serve, for example, in reducing or eliminating noise associated with the DC voltage of the tile electronic components.

The choice of two rows of tiles 90 on a module 100 in the present example is preferred as it provides at least one free edge for each tile 90, thus facilitating tile replacement and, at the same time, providing enough space at the region 104 for mounting the electronic components 106. It should, however, be noted that a number of rows of tiles 90 other than two could be used in other embodiments.

In this example, the tiles 90 are arranged electrically and electronically grouped in clusters 114 such that individual tiles within each cluster are readout in series only. The individual clusters 114 can be grouped together to form so-called megaclusters 116 so that all tiles in a megacluster are effectively readout serially. Separate megaclusters are then readout in parallel. The conductive paths from the tile location contacts to the electronic circuitry are formed by conductive tracks on layers in the multilayer circuit board 102. Connections between layers are provided by plated through holes in accordance with conventional multilayer circuit board technology. Sensitive signals are allocated a separate layer within the circuit board and can be shielded by shielding layers.

In the example implementation of FIG. 8c, each cluster 114 comprises three tiles and there are a total of eight such clusters. Specifically, tiles 171, 172, 173 are cascaded in cluster 201, tiles 174, 175, 176 are cascaded in cluster 202, tiles 177, 178, 179 are cascaded in cluster 203, tiles 180, 181, 182 are cascaded in cluster 204, tiles 183, 184, 185 are cascaded in cluster 205, tiles 186, 187, 188 are cascaded in cluster 206, tiles 189, 190, 191 are cascaded in cluster 207 and tiles 192, 193, 194 are cascaded in cluster 208.

Clusters 201 to 208 are then paired to form four megaclusters 116 of six tiles each, the six tiles within a megacluster being read in series and the four megaclusters in parallel. Specifically, clusters 201, 202 form one megacluster 210, clusters 203, 204 form another megacluster 212, clusters 205, 206 form another megacluster 214 and clusters 207, 208 form another megacluster 216.

In another example implementation, the clusters 201, 204, 205 and 208 are deactivated and only clusters 202, 203, 206 and 207 are active. The imaging area can thus be reduced to increase readout speed by effectively reading only three tiles in series. The choice between large or small imaging areas, is implemented electronically by means of switches in the electronic circuitry 106 and does not require any dismounting of the imaging tiles 90.

In a specific implementation of the module 100 of FIG. 8, the tiles 90 provide an imaging area of, approximately, 18.13×9.85 mm. The pixel pitch, excluding some edge pixels is 35 micrometers. There are 256 rows and 512 columns of pixels, hence a total of 131,072 pixels per tile. The detector substrate extends beyond the edges of the readout substrate chip except for side near region 92 of tile (see FIG. 7). Hence, the detector layers can be brought into physical and mechanical contact along the upper and lower edges of the module 100 as seen in FIG. 8b. In other words, the edges 120 of the detector substrates of adjacent tiles on a module 100 and adjacent tiles of a cassette, when modules are arranged side by side in a cassette, can be in physical (mechanical) contact.

The extent by which the detector substrate 44 extends beyond the readout substrate 42 on edges except edge 92 is determined by the precision with which the detector edges are themselves defined. Thus, the detector substrate edges are preferably defined to a high precision, for example 200 micrometer precision. In this case, the detector substrate extends beyond the readout substrate by at least this amount. More preferably, the precision should be 100 micrometers and the detector substrate extends beyond the readout substrate edges by at least this amount. Even more preferably, the precision should be 50 micrometers and the detector substrate extends beyond the semiconductor substrate edges by at least this amount. Even more preferably, the precision should be 10 micrometers and the detector substrate extends beyond the semiconductor substrate edges by at least this amount. Detector polishing can be employed to this end. It should be understood here that the references to the semiconductor substrate edges relate to at least the two edges adjacent to the region 92 and possibly to the edge at the opposite end of the imaging device 16 to the region 92.

In another example, a thin insulating film, for example a mylar film, is placed between adjacent detector surfaces in direct contact (i.e. at 120 in FIG. 8b). Preferably, this film has a thickness of 10 micrometers or less. More preferably, the film thickness is 5 micrometers or less. Yet more preferably, the film thickness is 1 micrometer or less.

Another example is configuring the modules 100 in an alternating up and down configuration with one module being offset relative to each of the or each immediately adjacent module along the direction perpendicular to the module plane by an amount slightly larger than the detector thickness. In this manner, the detector substrates 44 do not need to be in physical contact with one another, but rather they lie slightly under or over each other. The overlap of the detector substrates 44 needs to be no more than a few micrometers, typically less than 300 micrometers overlap. As the detector substrate thickness can typically be about 1 mm, the additional thickness required for the cassette is insignificant.

Other configurations and layouts are described in the Applicant's British patent application publication number GB 2 332 608A.

FIG. 9 is a cross-sectional view of a cassette which may be used to support one or more imaging devices or modules. This shows one module board 10 mounted on the module support structure 320 within a cassette 330 by means of screws 107 passing through the apertures 108 in the module board. Screws can be provided at one or both ends of the module board. Where screws are provided at one end of the board, an inter-engaging structure on the module support 320 for the other end of the board can be provided. The module support can be pre-threaded to receive the screws or can be secured by means of a separate nut. Spaces or other mechanisms can be provided for adjusting the relative position of the module and the module support in order, for example, to tilt the module to correct parallax error as described below. For example, adjustable mechanical supports can be provided to adjust the mechanical position and to correct detector angle from 5 to 2.5 degrees and to adjust all of the modules in a cassette at the same time at one end, or at both ends of the module array. Preferably, the apertures 108 in the modules are elongate as shown in FIG. 8 to facilitate adjustment of the modules and also to facilitate installation and removal of the modules. Thus, for example, to install a module in the middle of the module array, the fixing screws for the surrounding modules can be loosened and moved away from the position of the new module which can then be mounted, and the screws tightened. Subsequently, the surrounding modules can be moved back towards the newly installed module and the screws tightened. Similarly, to remove a centrally located module, the screws for mounting the surrounding modules can be loosened and moved away from the module to be removed.

External connections from the cassette to, for example, an external computer, are provided by means of a conventional external connector (for example a parallel connector) 354, which can be connected via a cable 356 to a computer. As the external connection via the cable 356 to a computer can be relatively long, the interface board 309 can include conventional amplification circuitry for transmission from the signals from the interface board to the computer and for reception of signals therefrom. Optionally, as described above, an USB or USB2 interface may be used.

It will be appreciated, that although the present embodiment is described as using screws for providing mechanical mounting of the modules, alternative mechanical arrangements such as clips, bayonet fittings and so on could be used. As a further alternative, combined electrical and mechanical arrangements such as zero insertion force connectors, plugs and sockets, could be used.

In the preferred embodiment of the invention, separate electrical connections are achieved by means of ribbons cables 111 which connect to cable connectors 109 provided on the module board 102. The ribbon cable connectors allow the electrical connection of the module 100 to an interface board 309.

In the preferred embodiment of the invention, an interface board 309, comprising power supplies, module system control electronics and a computer interface (optionally also with digital to analog converters) is placed near to one of the edges of the multi-module assembly 330. In this manner, an increase in the thickness of the cassette is avoided. The interface board forms part of or is contained with the imaging cassette.

FIG. 10 is a schematic external view of an imaging cassette 330, the cassette comprising an external housing 350, with an x-ray transmissive upper surface 352. FIG. 10 also shows the external connector 354. It will be noted that the external connector is provided on one end of the cassette which, in use, will be visible in the insertion slot 372 of X-ray apparatus 370. Thus, as shown in FIG. 10, the imaging cassette 330 is intended to replace a conventional X-ray film cassette for use in conventional X-ray equipment. Typically, the cassette will have a thickness of 20–30 mm and an external surface of, for example, 50×30 mm (eg, for dental panoramic imaging), 180×240 mm (eg, for mammography) or 400×400 mm (eg, for chest x-rays).

The total readout time for a cassette depends on the pixel readout/switching rate and the number of tiles on the cassette. In the preferred embodiment of the invention, the output for a megacluster is derived by multiplexing cluster outputs in circuitry 106 in the region of the module identified at 104 in FIG. 8b. The overall output rate is increased by a factor equal to the number of megaclusters. In the example implementation described with reference to FIG. 8c, there are four megaclusters. Accordingly, for a pixel readout/switching rate of 5 MHz, the module output rate is 20 MHz. With 144 tiles in the full cassette of FIG. 7, the total number of pixels approaches 18.9 million. Accordingly, for pixel switching rates of 2.5, 5.0, 10.0 MHz, the total approximate readout times are 7.5 seconds, 3.8 seconds and 1.9 seconds, respectively. If only half of the tiles are selected for readout, the readout time is halved for the same clock rate. Preferably, the pixel switching rate should be 2.5 MHz or higher. More preferably, the pixel switching rate should be 5 MHz or higher. Even more preferably, the pixel switching rate should be 10 MHz or higher. Yet more preferably, the pixel switching rate should be 20 MHz or higher.

In an embodiment of the invention, the analog multiplexed outputs from each module are further multiplexed in the cassette. In the example implementation of FIG. 9, the analog outputs from each of the six modules are fed into four analog multiplexers on the interface board 309 and the resulting four signals, representing combinations of module output signals, are digitized. The digitisation can be effected by feeding the outputs from the interface board on a multichannel ADC in the control electronics of a computer (for example control electronics as in FIG. 2). Optionally, video digitisation can be employed.

Thus, in an embodiment of the invention the cassette 330 could provide the imaging array 15 of a system as shown in FIG. 2.

In one embodiment, the control electronics has four modes of operation for selecting the area of the imaging substrate which is to be active. FIG. 11 illustrates the active area of the imaging substrate for each of the four modes of operation, 0,0; 0,1; 1,0 and 1,1. The control electronics has two operating mode signal inputs mode 0 and mode 1, which can be set in various combinations of high and/or low in order to select one of the four operating modes in the active area of the imaging substrate. An area of an imaging substrate is made active or non-active merely by reading out from an image or pixel cell circuit (active area) or not reading out from an image or pixel cell circuit (non-active area).

The imaging device illustrated in FIG. 11 has rows which are 1.8 cm long, columns which are 1.08 cm long, and pixel cell pitch of 100 μm.

FIG. 11 illustrates the four modes of operation. The table illustrated in FIG. 12 summarises the operating modes. When both mode and signals are low, the imaging device is operated in normal mode with the whole chip being scanned starting from the first row and finishing at the last row, row 108. A row_out signal is asserted once the scanning has reached the end of row 108. This first mode is known as the "normal mode", and is established by asserting the numbers 0,0 on the mode 1, mode 0 inputs.

When mode 1 is low and mode 0 is high, 80 rows from the middle of the imaging device are used. This results in an 8 mm wide active area of the imaging device being established. Consequently, this mode is named the "8 mm window" mode. Scanning starts from the first image or pixel cell in row number 15 and a row_out signal is established after reaching the end of row number 94.

When mode 1 is high and mode 0 is low, 60 rows from the middle of the imaging device are active, and the scanning starts from the first image or pixel cell in row number 25 and finishes at the end of row number 84 at which point a row_out signal is established. This mode is named the "6 mm window" mode.

When both mode signals are high, 40 rows from the middle of the imaging device are active, and the scanning starts from the first image or pixel cell in row number 35 and finishes after reaching the end of row number 74, whereupon a row_out signal is established. This mode is named the "4 mm window" mode.

In the normal operating mode, the read-out sequence of the imaging device starts with the first image or pixel cell of the first row shown in the upper left hand corner of the imaging device illustrated in FIG. 11. This is initiated by an enable pulse being asserted on both the col_ena and row_ena signal lines. On the next clock cycle, the next image or pixel cell on the same row is selected by selecting the next column and so on and so forth until the last column of the first row is reached. Then at a col_out signal is asserted. A new pulse is asserted on the col_ena input, and the first image or pixel cell of the second cell is read. At the end of the last row, a row_out pulse is asserted. The timing diagram for an imaging chip operating in the normal mode is illustrated in FIG. 13.

The above described embodiment is particularly suitable for imaging apparatus and assemblies where the X-ray beam is very narrow, for example dental panoramic imaging systems utilizing a fan shaped X-ray beam. The pixel or imaging cell addressing is done column by column. The operating modes described above may be selected according to the X-ray beam width of the imaging system. For example, if the width of the X-ray beam is 4 mm or less, then the mode can be set so that the imaging device operates in the 4 mm window mode. Thus only a 4 mm wide strip for the centre of the imaging device is read. This results in less image or pixel cell circuits having to be read thereby reducing the data to be processed and transferred from the imaging device. This results in increased frame rate, or reduced data bandwidth requirements. The number of operating modes is not limited to four, the modes described above merely being illustrative examples. Four or fewer modes may be implemented. Furthermore, it will be evident to a person skilled in the art that the arrangement of different operating modes providing different active areas for the imaging device is not limited to the particular imaging device or configuration described with reference to FIGS. 11 to 13, but may be applied to other configurations, for example, such as those described with reference to FIGS. 5 through 8.

A particular embodiment is illustrated in FIG. 14 in which the detection area comprises eight imaging devices 90, mounted on a support 108. Such an embodiment is particularly suitable for dental panoramic imaging applications in which a relatively narrow X-ray beam is utilized, for example a fan beam or cone beam. The configuration may also be utilized in a system for in-line non-destructive testing in which objects to be tested are moved relative to the imaging devices, for example along a conveyor belt. Each imaging device 90 may be individually readout, which would require there to be eight separate readout channels coupled to the image processor 28. For such an independently operable configuration, the column and row enable signals are fed back to form a closed loop system such as is illustrated in FIG. 15 of the drawings. The operation of the device illustrated in FIG. 15 starts with an enable signal being asserted. Once started, the first row and the first column of the imaging device 90 are selected for output. A column selector advances at each clock cycle to sequentially read the columns, and when the last column of the first row is read, a col_out signal is produced. The col_out signal is fed back to logic circuitry 380/382, and the row selector is advanced. The following rows are read in the same way until the last row of the imaging device 90 is reached and the row_out signal is given a pulse which is fed back to enable the first column of the device 90.

FIG. 16 illustrates an example for connecting two tiles such that they are read out sequentially as one unit. Again, imaging is started using the enable signal input to logic circuitry 380/382. Once started, the first row and the first column of the first imaging device 90a are selected for output. The column selector advances at each clock cycle and when the last column of the first row is read, a col_out signal is produced. The col_out signal is connected to the col_ena input of the next imaging device 90b. The reading of pixels is continued from the first row of imaging device 90b and so on until the last pixel in the first row of the whole imaging area defined by 90a and 90b is read. The col_out signal of imaging device 90b is connected back to imaging device 90a, and the row selector is advanced. The following rows are read in the same way until the last row of the imaging device is reached and the row_out and last-pixel is given a pulse which indicates the last pixel in the imaging area has been reached, and is fed back to enable the first column of imaging device 90a. Evidently, if the enable signal in either the schematics illustrated in FIG. 15 or FIG. 16 should go low, then scanning is stopped.

Referring now to FIG. 17, there is schematically illustrated a dental panoramic imaging system 500 in accordance with an embodiment of the present invention. The imaging system 500 comprises an X-ray source 502 and a sensing device 503 arranged around a patient's head 512. The sensing device, 503, may comprise a single imaging device or a number of imaging devices mounted to form an imaging module such as respectively described above with reference to FIG. 8 and FIG. 14 of the drawings. Suitably, the imaging device or imaging device modules are mounted in a cassette such as described above with reference to FIGS. 9 and 10 of the drawings. Such a cassette may then be mounted in a suitable support mount, and preferably in a mount to be used for supporting a film cassette. Thus, the imaging cassette forming the sensor device 503 can be interchangeable with a film cassette.

Control electronics 506 include processing and control circuitry for the imaging device or imaging device modules forming sensor device 503, and are connected to the cell circuits of the semi-conductor substrate as represented schematically by the two way connection 504. The control electronics 506 control the imaging device/s in a similar manner to that previously described above. The control electronics 506 are further interfaced by a path represented schematically by arrow 508 to an image processor 510. The image processor 510 operates as described above, and includes data storage in which it stores digital values representative of the charge read from each image cells, and stored in a frame store corresponding to the image frame that is currently being accumulated.

X-ray source 502 and sensor device 503 are arranged to rotate about a point 514, the point of rotation 514 itself being moveable in order to image a particular or desired plane of the object 512 on the sensor device 503.

In operation, the imaging system 500 is first initialised prior to a scan. For example, a sensor calibration routine may be undertaken to measure dark or quiescent current for example in order to subtract these values from the charge values read out during scanning. At the start of the scan the X-ray source is at the first position 502(a), with the sensor device at a corresponding first position 503(a). An X-ray fan beam 516(a) is output from X-ray source at position 502(a) and illuminates the patient's head 512 to form an image on the sensor element 503 of a portion 518(a) of the patient's head 512.

Both X-ray source 502 and sensor device 503 continuously move during the scan motion. By "continuous" it is meant that neither the X-ray source 502 or sensor device 503 step through each stage of the scan, with a particular exposure taken for each stage. Rather, their movement is smooth. However, it will be readily appreciated by the person of ordinary skill in the art that such a smooth motion may be imparted to either one or both of the X-ray source and sensor device by way of a stepper motor, for example, appropriately clocked at a frequency to provide a substantially continuous motion. Additionally, X-ray source 502 may be left to radiate continuously throughout the scan, rather than operated to take separate exposures for each step in a stepped scanning motion. Thus, it is possible to undergo scanning in 10 seconds or less, compared to conventional stepping systems which can take around 20 seconds. Furthermore, because the X-ray source is left to run continuously during the scan, it does not undergo rapid switching on and off which can substantially reduce the lifetime of the X-ray source. In order to avoid blurring of the image 516(a) of object part 518(a) charge values corresponding to X-rays incident on a detector cell should be read out at time intervals which are substantially less than or equal to the time taken for an image point corresponding to an object point in a patient's head traversing half a detector cell width of an imaging device forming the sensor device 503. Within such a time interval, all of the image cell output values of the image cells of the devices used for performing the scan are read out. The image cell output values read out of the all the image cells used for the scan at each of these time intervals form image frames. Each image frame can be stored in the image processor, and later combined with other image frames in order to produce an image. Thus, the first image frame takes an image of part 518(a) of a patient's head. At the next interval for which all the image cell output values have been read out, i.e. frame interval, an image 516(b) of part 518(b) of a patient's head corresponding to an X-ray source position 502(b) is stored as an image frame. This process continues until scanning has been completed.

The rate at which individual cells have to be read out in order that the whole frame is read out during the time period it would take an image point to traverse no more than half a detector cell depends upon the speed at which the X-ray source and sensor device are moving, together with the number of imaging cells of the imaging devices that are being utilised. For example, using imaging devices in accordance with the embodiments illustrated in FIG. 11 different imaging cells can be used depending upon the operating mode for the imaging device. Evidently, the fewer the imaging cells being utilised, the slower each imaging cell may be clocked to read out the image cell output value. Suitably the clock rate is 5 MHz or more, preferably 10 MHz or more and more preferably 20 MHz or more. The readout clock rate can be determined by setting the control electronics 506 to an appropriate mode depending upon the mode of operation of the imaging device together with the speed of movement of the X-ray source and sensor device.

Referring now to FIG. 18 there is schematically illustrated an example of an automated X-ray testing system 524 for the non-destructive testing of objects 513 such as circuit boards. In the example illustrated in FIG. 18 both the X-ray source 502 and sensor device 503 remain stationary. The sensor device is coupled to control electronics 506 schematically illustrated by two-way arrow 504. The image processor 510 is coupled to the control electronics as schematically illustrated by arrow 508. A fan X-ray beam 516 is omitted from X-ray source 502 to be incident on sensor device 503. Objects to be tested or inspected are placed on a conveyor belt 522 which passes them through the X-ray fan beam 516. In this embodiment, it is the movement of the object 513 which provides scanning motion. Scan images are formed in the same manner as described with reference to FIG. 17. That is to say, individual image cell output values are read out at clock rates such that all the image cells being utilised can be read out within the time interval for image point to travel no more than one half of a detectors width. This avoids blurring of the image, and maintains a pixel level resolution.

Embodiments in accordance with the present invention can provide frame rates of 60 frames per second or more, preferably 100 frames per second or more and more preferably 200 frames per second or more.

For embodiments in which the outputs of a group of cells are combined for applications where a lower resolution is necessary, or where only charge output values for one imaging cell of a group of cells is utilised, for example to reduce data readout rates, then all relevant readout operations must take place within or equal to a time interval corresponding to an image point traversing half the distance across a group of cells whose outputs are being combined, or for which the output from only one cell is being utilised.

In view of the foregoing description it will be evident to a person skilled in the art that various modifications may be made within the scope of the invention. For example, although a dental panoramic imaging system has been illustrated, other imaging configurations may utilise the invention, for example whole body scanners.

The scope of the present disclosure includes any novel feature or combination of features disclosed therein either explicitly or implicitly or any generalisation thereof irrespective of whether or not it relates to the claimed invention or mitigates any or all of the problems addressed by the present invention. The applicant hereby gives notice that new claims may be formulated to such features during the prosecution of this application or of any such further application derived therefrom. In particular, with reference to the appended claims, features from dependent claims may be combined with those of the independent claims and features from respective independent claims may be combined in any appropriate manner and not merely in the specific combinations enumerated in the claims.

For the avoidance of doubt, the term "comprising" used in the description and claims should not be construed to mean only "consisting only of".

The invention claimed is:

1. An imaging system for high energy radiation direct conversion scan imaging, comprising:
 a high energy radiation source member;
 a semiconductor high energy radiation direct conversion imaging device, including a plurality of individually addressable imaging cells, each imaging cell comprising a detector cell and a readout cell for producing individual imaging cell output values representative of high energy radiation incident on said detector cell, said imaging device comprising an imaging area, having a length and a width comprising plural rows and columns of imaging cells, each extending generally orthogonally to the direction of radiation transmission, and a thickness, extending generally in the direction of radiation transmission, which is substantially shorter than both said length and said width;

said source member and/or said imaging device arranged to move substantially continuously relative to an object position for scanning an object at said object position; and wherein said readout cells are arranged to readout said individually addressable imaging cell output values at time intervals substantially corresponding to an object image point traversing half the distance or less of a detector region in the scanning direction during a scan.

2. An imaging system according to claim 1, arranged to read out an image cell value from each of a subset of said plurality of imaging cells during each of said time intervals.

3. An imaging system according to claim 1, wherein said source member and/or said imaging device are moveable to image a part of an object in said object position from two or more positions.

4. An imaging system according to claim 1, wherein said source member and/or said imaging device are arranged to rotatably move relative to said object position.

5. An imaging system according to claim 4, said source member and/or said imaging device are rotatably moveable about a moveable axis of rotation.

6. A dental panoramic imaging system comprising an imaging system according to claim 1.

7. An imaging system according to claim 6, which is arranged to provide imaging data for generating plural tomographic image planes of an object from a single imaging scan operation.

8. An imaging system according to claim 6, which is arranged to provide imaging data for performing a dental panoramic reconstruction, comprising plural sharp layers following the center line of teeth in a skull, from a single imaging scan operation.

9. An imaging system according to claim 6, which is arranged to provide imaging data for performing reconstruction of plural different dental arch configurations, from a single imaging scan operations.

10. An imaging system according to claim 6, which is arranged to provide imaging data for constructing plural images, each comprising a sharp layer of different depth and profile, by shifting and adding several stored image frames taken from a single imaging scan operation.

11. A dental computerised tomography imaging system comprising an imaging system according to claim 1.

12. An imaging system according to claim 11, which is arranged to provide imaging data for generating plural tomographic image planes of an object from a single imaging scan operation.

13. An imaging system according to claim 11, which is arranged to provide imaging data for performing a dental panoramic reconstruction, comprising plural sharp layers following the center line of teeth in a skull, from a single imaging scan operation.

14. An imaging system according to claim 11, which is arranged to provide imaging data for performing reconstruction of plural different dental arch configurations, from a single imaging scan operations.

15. An imaging system according to claim 11, which is arranged to provide imaging data for constructing plural images, each comprising a sharp layer of different depth and profile, by shifting and adding several stored image frames taken from a single imaging scan operation.

16. An imaging system according to claim 1, for in-line high energy radiation inspection system, wherein said source member and/or said imaging device are arranged for linear movement relative to said object position.

17. An imaging system according to claim 1, wherein said source member comprises a support for a high energy radiation source.

18. An imaging system according to claim 1, wherein said source member comprises a high energy radiation source.

19. An imaging system according to claim 17, wherein said high energy radiation source comprises a steerable beam high energy radiation source.

20. An imaging system according to claim 19, wherein said steerable beam high energy radiation source comprises an electrically steerable beam.

21. An imaging system according to claim 17, wherein said high energy radiation source is operated to continuously radiate said high energy radiation during said scanning.

22. An imaging system according to claim 1, wherein said imaging device is arranged to readout said imaging cell output values at time intervals corresponding to an object image point traversing a part of said detector region.

23. An imaging system according to claim 22, wherein said imaging device is arranged to readout said imaging cell output values at time intervals substantially corresponding to an object image point traversing half a detector region.

24. An imaging system according to claim 1, wherein said readout cell is arranged to readout said imaging cell output values during said traversing of said detector region.

25. An imaging system according to claim 24, wherein said readout cells are arranged to readout said imaging cell output values substantially continuously during said traversing of said detector region.

26. An imaging system according to claim 1, wherein said detector region comprises a detector cell.

27. An imaging system according to claim 1, wherein said readout cells are arranged to readout said imaging cell output values after said traversing.

28. An imaging system according to claim 1, wherein said readout cells are arranged to readout said imaging cell output values at a rate of substantially 5 MHz or more.

29. An imaging system according to claim 28, wherein said readout cells are arranged to readout said imaging cell output values at a rate greater than 10 MHz.

30. An imaging system according to claim 29, wherein said readout cells are arranged to readout said imaging cell output values at a rate of 20 MHz or more.

31. An imaging system according to claim 1, wherein said imaging device is arranged to readout imaging cell output values for at least some of said plurality of imaging cells of said imaging device.

32. An imaging system according to claim 1, comprising a plurality of imaging devices.

33. An imaging system according to claim 32, wherein each of said plurality of imaging devices are readout individually.

34. An imaging system according to claim 32, wherein two or more imaging devices are coupled together for reading out said imaging cell output values from more than one imaging device.

35. An imaging system according to claim 1, interfaceable to data acquisition and control apparatus for receiving and storing imaging cell output values.

36. An imaging system according to claim 35, wherein said data acquisition and control apparatus comprises a personal computer.

37. An imaging system according to claim 36, interfaceable to said personal computer, or to a notebook or to a laptop computer using an USB interface bus.

38. An imaging system according to claim 36, interfaceable to said personal computer, or to a notebook or to a laptop computer using an USB2 interface bus.

39. An imaging system according to claim 1, said readout cells comprising high speed integrated circuitry.

40. An imaging system according to claim 39, said readout cells comprising circuitry fabricated in accordance with one or more of the following technologies:
CMOS; Double Poly MOS; NMOS; JFET; P2CMOS; XMOS; GaAs integrated circuit processes; ECL; TTL; Bipolar Linear; BiCMOS; EEPROM/PLASH process; SALICIDE process; OP to electronics; Complementary Bipolar DLM2; Copper Fine Line; and BCD C Bipolar/CMOS/DMOS.

41. An imaging system according to claim 1, wherein said imaging device is arranged to readout the imaging cell output values at a frame rate of 60 frames/second.

42. An imaging system according to claim 1, wherein said imaging device is arranged to readout the imaging cell output values at a frame of 200 frames/second.

43. An imaging system according to claim 1, wherein said imaging device is arranged to readout the imaging cell output values at a frame rate of 200 frames/second.

44. An imaging system according to claim 1, wherein the thickness of the imaging device substantially comprises the combined thickness of a detector cell and a readout cell, which are arranged one above the other in the direction of radiation transmission.

45. An imaging system according to claim 1, wherein the scanning direction is substantially along a width axis of the imaging device.

46. An imaging system according to claim 1, which is arranged to provide imaging data for generating plural tomographic image planes of an object from a single imaging scan operation.

47. A method of high energy radiation direct conversion scan imaging using an imaging system including:
a high energy radiation source member; and
a semiconductor high energy radiation direct conversion imaging device including a plurality of individually addressable imaging cells, each imaging cell comprising a detector cell and a readout cell for producing imaging cell output values representative of high energy radiation incident on said detector cell, said imaging device comprising an imaging area, having a length and a width comprising plural rows and columns of imaging cells, each extending generally orthogonally to the direction of radiation transmission, and a thickness, extending generally in the direction of radiation transmission, which is substantially shorter than both said length and said width;
the method comprising:
moving said source member and/or said imaging device substantially continuously relative to an object position for scanning an object of said object position; and reading out imaging cell output values at time intervals substantially corresponding to an object image point traversing half the distance of a detector region in the direction of scanning.

48. A method according to claim 47, wherein said reading out step includes reading out an image cell value from each of a subset of said plurality of imaging cells during each of said time intervals.

49. A method according to claim 47, wherein said step of moving comprises moving said source member and/or imaging device to image a part of an object in said object position from two or more positions.

50. A method according to claim 47, further comprising arranging said source member and/or said imaging device to rotatably move relative to said object position.

51. A method according to claim 50, wherein said source member and/or said imaging device are arranged for a rotatable movement about a movable axis of rotation.

52. A method according to claim 47, wherein said high energy radiation source member comprises a high energy radiation source continuously operated to radiate high energy radiation during scanning.

53. A method according to claim 47, wherein said step of reading out comprises reading out imaging cell output values at time intervals corresponding to an object image point traversing a part of said detector region.

54. A method according to claim 47, wherein said step comprises reading out imaging cell output values at time intervals substantially corresponding to an object image point traversing half of a detector region.

55. A method according to claim 47, wherein said step of reading comprises reading out imaging cell output values during said traversing of said detector region.

56. A method according to any one of claim 47, wherein said detector region comprises a detector cell.

57. A method according to claim 47, wherein said step of reading comprises reading image cell output values for at least some of said plurality of imaging cells of said imaging device.

58. A method according to claim 47, for an imaging system including a plurality of imaging devices, and wherein said step of reading comprises reading each of said plurality of imaging device individually.

59. A method according to claim 47, for an imaging system comprising a plurality of imaging devices having two or more imaging devices coupled together, and wherein said step of reading comprises reading out image cell output values from more than one imaging device.

60. A method according to claim 47, including the step of providing imaging data for performing a dental panoramic reconstruction, comprising plural sharp layers following the center line of teeth in a skull, from a single imaging scan operation.

61. A method according to claim 47, including the step of providing imaging data for performing reconstruction of plural different dental arch configurations, from a single imaging scan operation.

62. A method according to claim 47, including the step of providing imaging data for constructing plural images, each comprising a sharp layer of different depth and profile, by shifting and adding several stored image frames taken from a single imaging scan operation.

63. An imaging system for high energy radiation direct conversion scan imaging, which is arranged to provide imaging data for generating plural tomographic image planes of an object from a single imaging scan operation, comprising:

a high energy radiation source member;

a semiconductor high energy radiation direct conversion imaging device including a plurality of imaging cells, each imaging cell being individually addressable and comprising a detector cell and a readout cell for producing imaging cell output values representative of high energy radiation incident on said detector cell;

said source member and/or said imaging device arranged to move substantially continuously relative to an object position for scanning an object at said object position; and wherein said readout cells are operable to readout said individually addressable imaging cell output values at time intervals substantially corresponding to an object image point traveling half the distance or less of a detector region in the scanning direction during a scan.

64. A method of high energy radiation direct conversion scan imaging using an imaging system, which is arranged to provide imaging data for generating plural tomographic image planes of an object from a single imaging scan operation, the system including:

a high energy radiation source member;

and a semiconductor high energy radiation direct conversion imaging device including a plurality of image cells, each imaging cell being individually addressable and comprising a detector cell and a readout cell for producing imaging cell output values representative of high energy radiation incident on said detector cell;

the method comprising:

moving said source member and/or said imaging device substantially continuously relative to an object position for scanning an object of said object position; and reading out individually addressable imaging cell output values at time intervals substantially corresponding to an object image pointy traversing half the distance of a detector region in the direction of scanning.

* * * * *

UNITED STATES PATENT AND TRADEMARK OFFICE
CERTIFICATE OF CORRECTION

PATENT NO. : 7,136,452 B2
APPLICATION NO. : 10/024037
DATED : November 14, 2006
INVENTOR(S) : Konstantinos E. Spartiotis et al.

It is certified that error appears in the above-identified patent and that said Letters Patent is hereby corrected as shown below:

| Column | Line | |
|---|---|---|
| 2 | 1 | After ""(i.e." insert --,--. |
| 2 | 3 | Change "X-rays." to --X-rays).--. |
| 2 | 33 | Change "result" to --results--. |
| 3 | 14 | Change "placed either" to --placed at either--. |
| 3 | 26 | After "395" delete ")". |
| 4 | 49 | Change "device. In" to --device, in--. |
| 5 | 19 | Change "multi slice" to --multi-slice--. |
| 5 | 36 | Change "old fashioned" to --old-fashioned--. |
| 5 | 46 | Change "on line" to --online--. |
| 5 | 48 | Change "CCD based" to --CCD-based--. |
| 5 | 57 | After "additionally" insert --,--. |
| 6 | 4 | Change "CCD's or" to --CCDs nor--. |
| 6 | 6 | After "invention" delete "to"; change "multi slice" to --multi-slice--. |
| 8 | 10 | Change "readout" to --read out--. |
| 8 | 39 | Change "Complimen-" to --Complemen- --. |
| 9 | 21 | Change "Devices" to --Device--. |
| 9 | 30 | Change "cell, values" to --cell, with values--. |
| 9 | 49 | Change "TIBr" to --TiBr--. |
| 11 | 41 | Change "24 is" to --24 are--. |

UNITED STATES PATENT AND TRADEMARK OFFICE
CERTIFICATE OF CORRECTION

PATENT NO. : 7,136,452 B2
APPLICATION NO. : 10/024037
DATED : November 14, 2006
INVENTOR(S) : Konstantinos E. Spartiotis et al.

It is certified that error appears in the above-identified patent and that said Letters Patent is hereby corrected as shown below:

| Column | Line | |
|---|---|---|
| 12 | 45 | Change "M14A52" to --M14A 452--. |
| 13 | 60 | Change "(PC)" to --(PCI)--. |
| 14 | 34 | After "used" delete "removable". |
| 16 | 30 | Change "preferably." to --preferably,--. |
| 16 | 49 | Delete "each of the or". |
| 28 | 15 | Change "pointy" to --point--. |

Signed and Sealed this

Eighth Day of April, 2008

JON W. DUDAS
*Director of the United States Patent and Trademark Office*

UNITED STATES PATENT AND TRADEMARK OFFICE
CERTIFICATE OF CORRECTION

PATENT NO. : 7,136,452 B2  Page 1 of 1
APPLICATION NO. : 10/024037
DATED : November 14, 2006
INVENTOR(S) : Konstantinos E. Spartiotis et al.

It is certified that error appears in the above-identified patent and that said Letters Patent is hereby corrected as shown below:

Title page, item [63] change "abandoned which is a continuation application of U.S." to --abandoned which is a divisional application of U.S.--

Signed and Sealed this

Eleventh Day of November, 2008

JON W. DUDAS
*Director of the United States Patent and Trademark Office*

UNITED STATES PATENT AND TRADEMARK OFFICE
CERTIFICATE OF CORRECTION

PATENT NO. : 7,136,452 B2
APPLICATION NO. : 10/024037
DATED : November 14, 2006
INVENTOR(S) : Konstantinos E. Spartiotis et al.

It is certified that error appears in the above-identified patent and that said Letters Patent is hereby corrected as shown below:

| Column | Line | |
|---|---|---|
| 1 | 11 | Change "abandoned which is a continuation application of U.S." to |
| | | --abandoned which is a divisional application of U.S.-- |

Signed and Sealed this

Ninth Day of June, 2009

JOHN DOLL
*Acting Director of the United States Patent and Trademark Office*